United States Patent
Yu et al.

(10) Patent No.: US 11,773,118 B2
(45) Date of Patent: Oct. 3, 2023

(54) METHODS OF MAKING HIGH ENANTIOSELECTIVE SECONDARY ALCOHOLS

(71) Applicant: OBI PHARMA, INC., Taipei (TW)

(72) Inventors: Cheng-Der Tony Yu, Taipei (TW); Yih-Huang Hsieh, Taipei (TW); Shu-Yi Lin, Taipei (TW); Chin-Sheng Chao, Taipei (TW); Yin-Cheng Hsieh, Taipei (TW); Ming-Tain Lai, Taipei (TW)

(73) Assignee: OBI PHARMA, INC., Taipei (TW)

( * ) Notice: Subject to any disclaimer, the term of this patent is extended or adjusted under 35 U.S.C. 154(b) by 206 days.

(21) Appl. No.: 17/432,668

(22) PCT Filed: Feb. 21, 2020

(86) PCT No.: PCT/US2020/019176
§ 371 (c)(1),
(2) Date: Aug. 20, 2021

(87) PCT Pub. No.: WO2020/172506
PCT Pub. Date: Aug. 27, 2020

(65) Prior Publication Data
US 2022/0106339 A1    Apr. 7, 2022

Related U.S. Application Data

(60) Provisional application No. 62/808,712, filed on Feb. 21, 2019.

(51) Int. Cl.
*C07F 9/24* (2006.01)
*C07C 231/14* (2006.01)

(52) U.S. Cl.
CPC .......... *C07F 9/2466* (2013.01); *C07C 231/14* (2013.01)

(58) Field of Classification Search
CPC ............................. C07F 9/2466; C07C 231/14
USPC ......................................................... 558/89
See application file for complete search history.

(56) References Cited

U.S. PATENT DOCUMENTS

| | | |
|---|---|---|
| 2005/0020632 A1 | 1/2005 | Grimler et al. |
| 2005/0032182 A1 | 2/2005 | Popp et al. |
| 2009/0192168 A1 | 7/2009 | Muci et al. |

FOREIGN PATENT DOCUMENTS

| | | |
|---|---|---|
| IN | DEL-2002-0039 A | 3/2007 |
| JP | 2003-533993 A | 11/2003 |
| TW | 201726695 A | 8/2017 |
| WO | WO2017/087428 A1 | 5/2017 |

OTHER PUBLICATIONS

International Preliminary Report On Patentability (IPRP) for PCT Patent App. No. PCT/US20/19176 (dated Sep. 2, 2021).
Ghanem, A. et al., "Application of Lipases in Kinetic Resolution of Racemates," CHIRALITY vol. 17, 2005; pp. 1-15.
Salunkhe, A. et al., "Highly Enantioselective Reduction of Prochiral Ketones with N,N-Diethylaniline-borane (DEANB) in Oxazaborolidine-catalyzed Reductions," Tetrahedron Letters 1997; 38(9); pp. 1523-1526.
Linder, T., "Synthetic Lignans Targeting Cardiovascular Diseases," Dissertation, Vienna University of Technology, 2016; 8 pp.
Huang, S., "Asymmetric Reduction of Acetophenone with Borane Catalyzed by Chiral Oxazaborolidinones Derived from L-Alpha-Amino Acids," Synthetic Communications 30(13); 2000; pp. 2423-2429.
Kim, C. et al., "Hydrolysis and Reverse Hydrolysis: Dynamic Kinetic Resolution," Comprehensive Chirality, vol. 7, 2012; pp. 156-180.
Sato, Y. et al., "Imidazopyridine derivatives as potent and selective Polo-like kinase (PLK) inhibitors," Bioorganic & Medicinal Chemistry Letters, vol. 19, 2009; pp. 4673-4678.
Traff, A., et al., "Asymmetric transformation of beta- and gamma-functionalized alcohols," 2011, Thesis; Stockholm University; pp. 1-37.
International Search Report and Written Opinion for PCT Patent App. No. PCT/US20/19176 (dated Jul. 15, 2020).

*Primary Examiner* — Kristin A Vajda
(74) *Attorney, Agent, or Firm* — Cermak Nakajima & McGowan LLP; Shelly Guest Cermak

(57) ABSTRACT

A new process to synthesis of compound OBI-3424 R-form and S-form products is provided. The "R-form" compound OBI-3423 was first synthesized with 48% overall yield from compound OBI-3424-5 by installation of the labile phosphate motif at later stage. The stereo chemistry is established by 5 steps chemo-enzyme combination synthesis to afford 99% optical purity. After then, the "S-form" compound OBI-3424 is prepared with improving overall yield of 54% from compound OBI-3424-5. The stereo chemistry is established by 4 steps combination of chemo-enzyme synthesis with excellent optical purity of 99%.

20 Claims, 4 Drawing Sheets

METHODS OF MAKING HIGH ENANTIOSELECTIVE SECONDARY ALCOHOLS

RELATED APPLICATION

This application is a national phase filing and claims priority under 35 U.S.C. § 371 to International Application No. PCT/US2020/019176, filed Feb. 21, 2020, and claims priority to U.S. Provisional Application Ser. No. 62/808,712 filed on Feb. 21, 2019, the entireties of which are hereby incorporated by reference herein for all purposes.

FIELD OF THE INVENTION

The present disclosure is related to synthesis and corresponding identification data of the compound OBI-3424 drug substance, which is designed as an anti-cancer small molecule prodrug.

BACKGROUND OF THE INVENTION

Cancer is one of the major causes of human morbidity and mortality. Cancer treatment is challenging because it is difficult to kill cancer cells without damaging or killing normal cells. Damaging or killing normal cells during cancer treatment is a cause of adverse side effects in patients and can limit the amount of anti-cancer drug administered to a cancer patient.

Aldo-keto reductase family 1 member C3 (AKR1C3) is an enzyme that, in humans, is encoded by the AKR1C3 gene. This gene encodes a member of the aldo/keto reductase superfamily, which consists of more than 40 known enzymes and proteins. These enzymes catalyze the conversion of aldehydes and ketones to their corresponding alcohols by utilizing NADH and/or NADPH as cofactors.

Many cancer cells overexpress AKR1C3 reductase relative to normal cells (e.g., Cancer Res. 2010, 70:1573-1584; Cancer Res. 2010, 66: 2815-2825). There remains a need for compounds suitable for treating cancer patients, including for selective AKR1C3 reductase activated prodrugs for treating cancer patients. The PCT patent application WO 2017/087428A1 disclosed a compound having the following Formula I or Formula II:

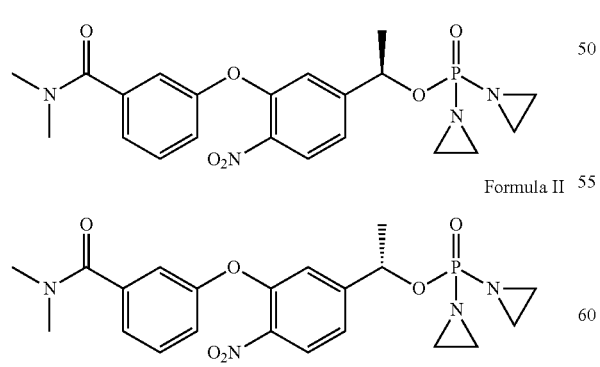

or a salt, isotopic variant, pharmaceutically acceptable solvate, or hydrate of each thereof. The said compound has an enantiomeric excess of no less than 80%, no less than 90%, or no less than 95%.

The PCT patent application WO 2019/062919A1 disclosed a compound (OBI-3424) and a method for treating leukemia. The properties of compound OBI-3424 were listed as Table 1.

TABLE 1

The properties of compound OBI-3424

OBI-3424

| | |
|---|---|
| Full Chemical Name | 3-[5-[(1S)-1-[bis(aziridin-1-yl(phosphoryloxy]ethyl]-2-nitrophenoxyl-N,N-dimethylbenzamide |
| Formula | $C_{21}H_{25}N_4O_6P$ |
| Molecular Weight | 460.43 g/mol |
| CAS number | 2097713-69-2 |

SUMMARY OF THE INVENTION

A purpose of the present disclosure is to provide a process for synthesis and corresponding identification data of the compound OBI-3424 drug substance, which is designed as an anti-cancer small molecule prodrug.

In one aspect, the present disclosure provides a method for preparing a compound of Formula 1, comprising:

Formula 1

$$\underset{R}{\overset{OH}{\bigwedge}}CH_3$$

step (1): reacting a compound of Formula 2 with a compound of Formula 3a in the presence of $BH_3$, B-Chlorodiisopinocampheylborane (DIP-Chloride), (S)-(−)-1,1'-Bi-2-naphthol, or $NaBH_4$; and Formula 2

$$\underset{R}{\overset{O}{\bigwedge}}CH_3$$

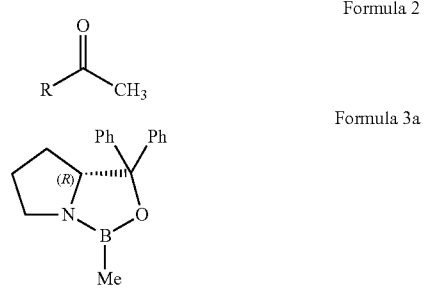

Formula 3a step (2): reacting a product of step (1) with:
 (A) lipase acrylic resin, $Na_2CO_3$, and one of isopropenyl acetate and 2,2,2-trifluoroethyl butyrate; or
 (B) protease, $Na_2CO_3$, and one of isopropenyl acetate and 2,2,2-trifluoroethyl butyrate; and reacting a product of step (B) with sodium methoxide in the presence of methanol, wherein R is

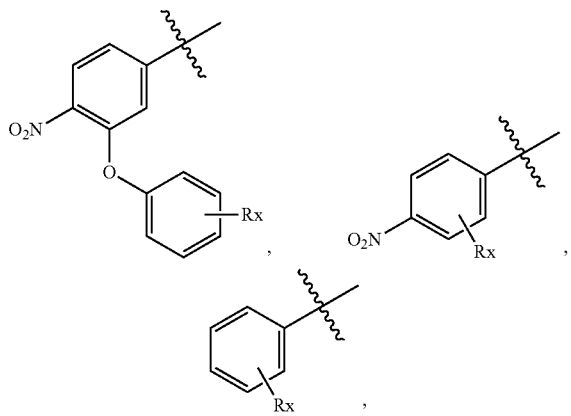

an aliphatic chain, or Rx;

wherein Rx is hydrogen, an unsubstituted or substituted cyclic ring group, an electron withdrawing group, or an electron donating group.

In another aspect, the present disclosure provides a method for preparing a compound of Formula 1, comprising:

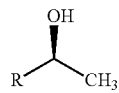

Formula 1 step (1a): reacting a compound of Formula 2 with a compound of Formula 3a in the presence of $BH_3$, DIP-Chloride, (S)-(−)-1,1'-Bi-2-naphthol, or $NaBH_4$;

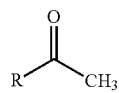

Formula 2

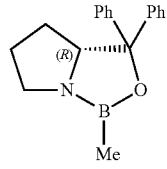

Formula 3a step (1b): reacting a product of step (1a) with acetic anhydride ($Ac_2O$); and step (2): reacting a product of step (1b) with:
(A) lipase acrylic resin, and $Na_2CO_3$; and reacting a product of step (A) with sodium methoxide in the presence of methanol; or
(B) protease, and $Na_2CO_3$, wherein R is

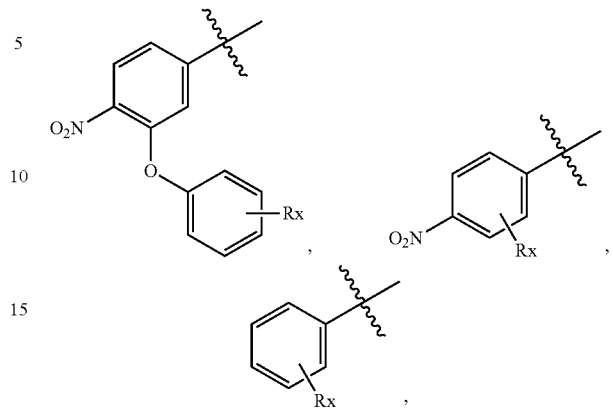

an aliphatic chain, or Rx;

wherein Rx is hydrogen, an unsubstituted or substituted cyclic ring group, an electron withdrawing group, or an electron donating group.

In yet another aspect, the present disclosure provides a method for preparing a compound of Formula 4, comprising:

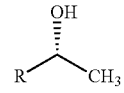

Formula 4 step (1): reacting a compound of Formula 2 with a compound of Formula 3b in the presence of $BF_3$, DIP-Chloride, (S)-(−)-1,1'-Bi-2-naphthol, or $NaBH_4$; and

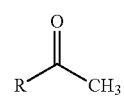

Formula 2

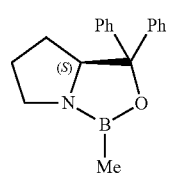

Formula 3b step (2): reacting a product of step (1) with:
(A) lipase acrylic resin, $Na_2CO_3$, and one of isopropenyl acetate and 2,2,2-trifluoroethyl butyrate; and reacting a product of step (A) with sodium methoxide in the presence of methanol; or
(B) protease, $Na_2CO_3$, and one of isopropenyl acetate and 2,2,2-trifluoroethyl butyrate, wherein R is

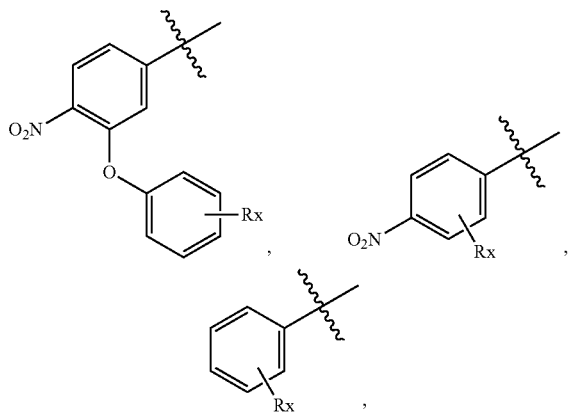

an aliphatic chain, or Rx;
wherein Rx is hydrogen, an unsubstituted or substituted cyclic ring group, an electron withdrawing group, or an electron donating group.

In still another aspect, the present disclosure provides a method for preparing a compound of Formula 4, comprising:

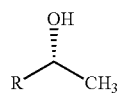

Formula 4 step (1a): reacting a compound of Formula 2 with a compound of Formula 3b in the presence of BH$_3$, DIP-Chloride, (S)-(−)-1,1'-Bi-2-naphthol, or NaBH$_4$;

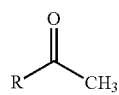

Formula 2

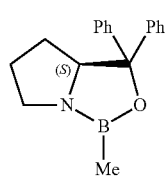

Formula 3b step (1b): reacting a product of step (1a) with acetic anhydride (Ac$_2$O); and
step (2): reacting a product of step (1b) with:
(A) lipase acrylic resin, and Na$_2$CO$_3$; or
(B) protease, and Na$_2$CO$_3$; and reacting a product of step (B) with sodium methoxide in the presence of methanol wherein R is

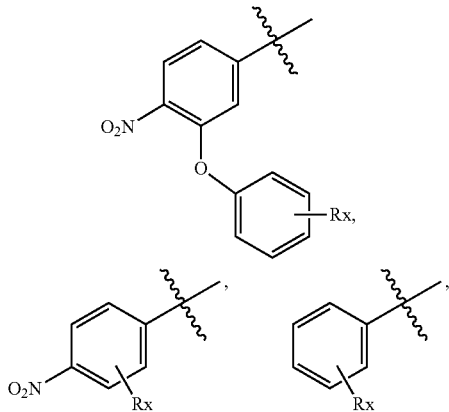

an aliphatic chain, or Rx;
wherein Rx is hydrogen, an unsubstituted or substituted cyclic ring group, an electron withdrawing group, or an electron donating group.

DETAILED DESCRIPTION

Definitions

Figure 1:
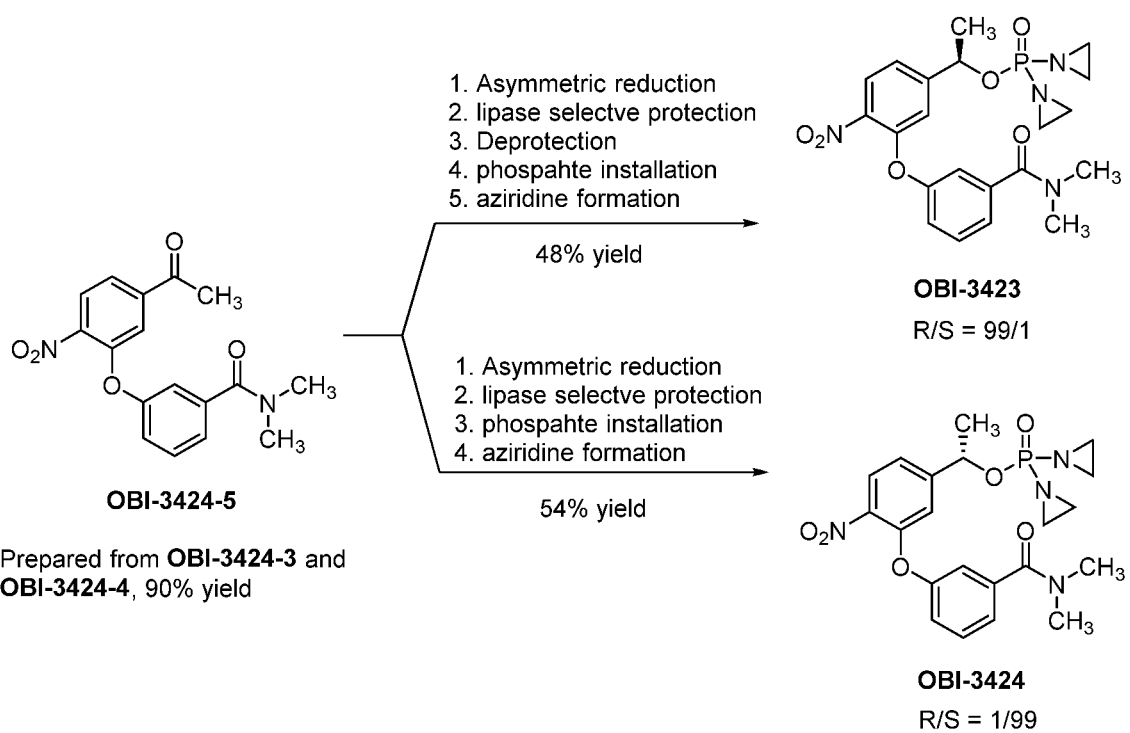
FIG. 1. Preparation of compound OBI-3423 (R-form) and compound OBI-3424 (S-form).

The following definitions are provided to assist the reader. Unless otherwise defined, all terms of art, notations, and other scientific or medical terms or terminology used herein are intended to have the meanings commonly understood by those skilled in the chemical and medical arts. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about". Reagents described herein are exemplary and equivalents of such may be known in the art.

"A," "an," and, "the" include plural referents unless the context clearly dictates otherwise. Thus, for example, reference to a compound refers to one or more compounds or at least one compound. As such, the terms "a" (or "an"), "one or more", and "at least one" are used interchangeably herein.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

The terms "optically active" and "enantiomerically active" refer to a collection of molecules, which has an enantiomeric excess (ee) of no less than about 10%, no less than about 20%, no less than about 30%, no less than about 40%, no less than about 50%, no less than about 60%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, no less than about 99.8%, or no less than about 99.9%. In certain embodiments, the enantiomeric excess for an optically or enantiomerically active compound is no less than about 90%, no less than about 95%, no less than about 98%, or no less than about 99%.

In describing an optically active compound, the prefixes R and S are used to denote the absolute configuration of the molecule about its chiral center. The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The terms "optically pure" and "enantiomerically pure" refer to a collection of molecules, which has an enantiomeric excess (ee) of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, no less than about 99.8%, or no less than about 99.9%. In certain embodiments, the enantiomeric excess for an optically or enantiomerically pure compound is no less than about 90%, no less than about 95%, no less than about 98%, or no less than about 99%. An enantiomeric excess of a compound can be determined by any standard methods used by one of ordinary skill in the art, including, but not limited to, chiral chromatography (gas chromatography (GC), high-performance liquid chromatography (HPLC), and thin-layer chromatography (TLC)) using an optically active stationary phase, isotopic dilution, electrophoresis, calorimetry, polarimetry, NMR resolution methods with chiral derivatization, and NMR methods with a chiral solvating agent or chiral shift reagent.

The terms "substantially pure" and "substantially homogeneous" mean sufficiently homogeneous to appear free of readily detectable impurities as determined by standard analytical methods used by one of ordinary skill in the art, including, but not limited to, thin-layer chromatography (TLC), gel electrophoresis (GE), high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single stereoisomer of a compound, as determined by standard analytical methods.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^1H$), deuterium ($^2H$), tritium ($^3H$), carbon-11 ($^{11}C$) carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, as example, or any carbon can be $^{13}C$, as example, or any nitrogen can be $^{15}N$, as example, and any oxygen can be $^{18}O$, where feasible according to the judgment of one of ordinary skill in the art. In certain embodiments, an "isotopic variant" of a compound contains unnatural proportions of deuterium.

The phrase "an isotopic variant thereof; or pharmaceutically acceptable salt, solvate, hydrate, or prodrug thereof" has the same meaning as the phrase "an isotopic variant of the compound referenced therein; or a pharmaceutically acceptable salt, solvate, or prodrug of the compound referenced therein."

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Patient," "subject," and "subject in need" are used interchangeably to refer to a mammal in need of treatment for cancer, particularly leukemia, more particularly T-cell acute lymphoblastic leukemia. Generally, the patient is a human. Generally, the patient is a human diagnosed with cancer. In certain embodiments a "patient," "subject," or "subject in need" may refer to a non-human mammal used in screening, characterizing, and evaluating drugs and therapies, such as a non-human primate, a dog, cat, rabbit, pig, mouse, or rat.

"Effective amount" used herein is referred to the amount of each active agent required to confer the desired effect on the subject, either alone or in combination with one or more other active agents. An effective amount varies, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

"Treating," "treatment of," or "therapy of" a condition or patient refers to taking steps to obtain beneficial or desired results, including clinical results. For purposes of this invention, beneficial or desired clinical results include, but are not limited to, alleviation or amelioration of one or more symptoms of cancer; diminishment of extent of disease; delay or slowing of disease progression; amelioration, palliation, or stabilization of the disease state; or other beneficial results. Treatment of cancer may, in some cases, result in partial response or stable disease.

"Pharmaceutically acceptable" component (such as a carrier or excipient) means that the compound or composition is suitable for administration to a subject to achieve the treatments described herein, without unduly deleterious side effects in light of the severity of the disease and necessity of the treatment. "Carrier" means a material that does not cause significant stimulation to an organism and does not eliminate the biological activity and characteristics of a given compound. "Excipient" means an inert substance added into a pharmaceutical composition to facilitate administration of a compound.

A usable pharmaceutically acceptable carrier, or excipient is disclosed in various references including *Handbook of Pharmaceuticals Excipients* edited by Raymond C Rowe, Paul J Sheskey, and Marian E Quinn. In an unlimited embodiment, said pharmaceutically acceptable carrier, or excipient can be selected from the group consisting of inert diluents, dispersing and/or granulating agents, surface active agents and/or emulsifiers, disintegrating agents, binding agents, preservatives, buffering agents, lubricating agents, and/or oils. Said compositions optionally further comprise at least one additional biologically active compound or agent.

The pharmaceutical composition might comprise, but not limited to, a single unit dose of the active ingredient (for instance, the compound of the present disclosure). For purposes of treatment, a dose unit can be in the form of a discrete article such as, but not limited to, a tablet or capsule, or can be a measurable volume of a solution, suspension or the like containing a unit dose of the active ingredient. The term "unit dose" herein refers to an amount of active ingredient intended for a single, but not limited to, oral, intravenous, intramuscular, cutaneous, subcutaneous, intrathecal, transdermal, implantation, sublingual, buccal, rectal, vaginal, ocular, otic, nasal, inhalation, or nebulization administration to a subject for treatment such as, but not limited to, alcohol dependence, opioid dependence, pain relief, or other diseases. The treatment may require periodic administration of unit doses of the compound of the present disclosure, for example, one unit dose two or more times a day, one unit dose with each meal, one unit dose every four hours or other interval, or only one unit dose per day.

EMBODIMENTS

In an embodiment, a method for preparing a compound of Formula 1 comprises the steps:

Formula 1 step (1): reacting a compound of Formula 2 with a compound of Formula 3a in the presence of BH$_3$, B-Chlorodiisopinocampheylborane (DIP-Chloride), (S)-(−)-1,1'-Bi-2-naphthol, or NaBH$_4$; and

Formula 2

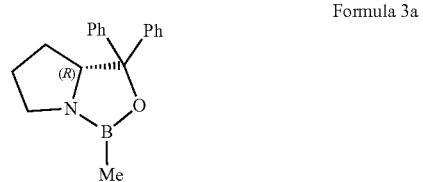

Formula 3a step (2): reacting a product of step (1) with:
  (A) lipase acrylic resin, Na$_2$CO$_3$, and one of isopropenyl acetate and 2,2,2-trifluoroethyl butyrate; or
  (B) protease, Na$_2$CO$_3$, and one of isopropenyl acetate and 2,2,2-trifluoroethyl butyrate; and reacting a product of step (B) with sodium methoxide in the presence of methanol,
wherein R is

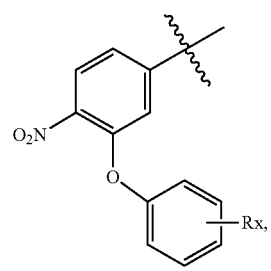

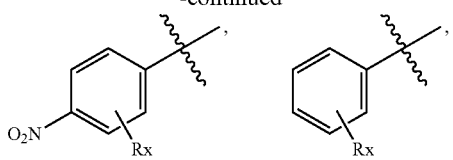

an aliphatic chain, or Rx;
wherein Rx is hydrogen, an unsubstituted or substituted cyclic ring group, an electron withdrawing group, or an electron donating group.

In an embodiment, the reaction can be shown as the following scheme:

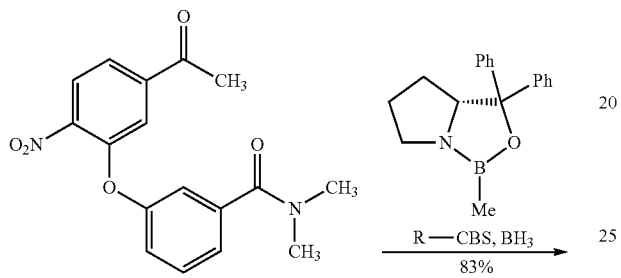

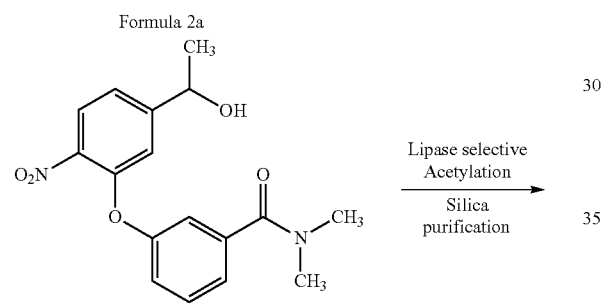

Formula 5
(S-form major)

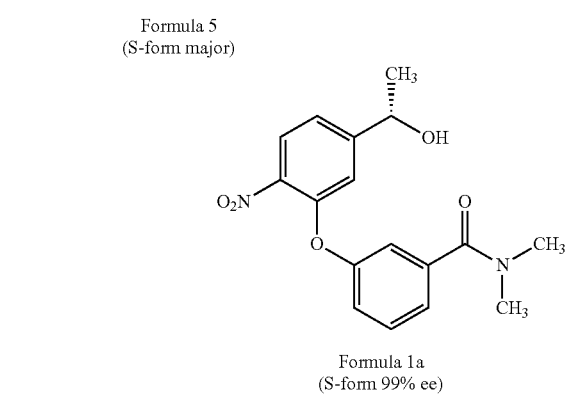

Formula 1a
(S-form 99% ee)

In an embodiment, a method for preparing a compound of Formula 1 comprises the steps:

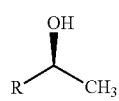

Formula 1 step (1a): reacting a compound of Formula 2 with a compound of Formula 3a in the presence of $BH_3$, DIP-Chloride, (S)-(−)-1,1'-Bi-2-naphthol, or $NaBH_4$;

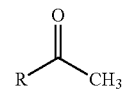

Formula 2

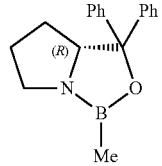

Formula 3a step (1b): reacting a product of step (1a) with acetic anhydride ($Ac_2O$); and step (2): reacting a product of step (1b) with:

(A) lipase acrylic resin, $Na_2CO_3$; and reacting a product of step (A) with sodium methoxide in the presence of methanol; or (B) protease, and $Na_2CO_3$, wherein R is

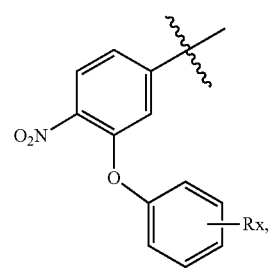

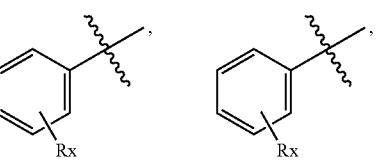

an aliphatic chain, or Rx;
wherein Rx is hydrogen, an unsubstituted or substituted cyclic ring group, an electron withdrawing group, or an electron donating group.

In an embodiment, the reaction can be shown as the following scheme:

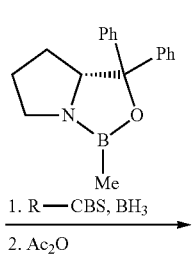

Formula 2a

-continued

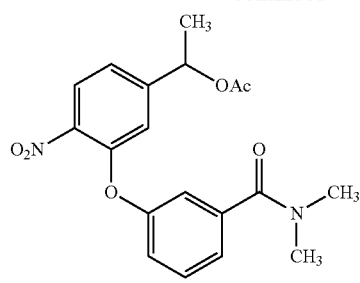

Formula 6
(S-form major)

Lipase/protease selective hydrolysis
silica purification

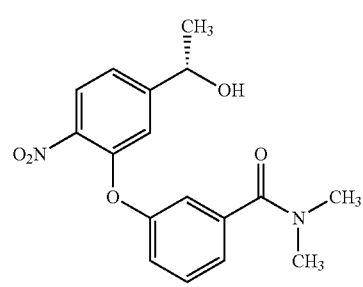

Formula 1a
(S-form 99% ee)

In an embodiment, a method for preparing a compound of Formula 4 comprises the steps:

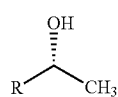

Formula 4 step (1): reacting a compound of Formula 2 with a compound of Formula 3b in the presence of $BH_3$, DIP-Chloride, (S)-(−)-1,1'-Bi-2-naphthol, or $NaBH_4$; and

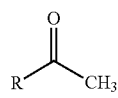

Formula 2

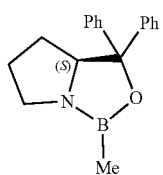

Formula 3b step (2): reacting a product of step (1) with:
(A) lipase acrylic resin, $Na_2CO_3$, and one of isopropenyl acetate and 2,2,2-trifluoroethyl butyrate; and reacting a product of step (A) with sodium methoxide in the presence of methanol; or
(B) protease, $Na_2CO_3$, and one of isopropenyl acetate and 2,2,2-trifluoroethyl butyrate, wherein R is

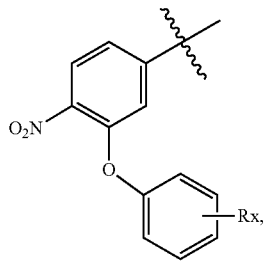

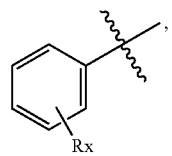

an aliphatic chain, or Rx;
wherein Rx is hydrogen, an unsubstituted or substituted cyclic ring group, an electron withdrawing group, or an electron donating group.

In an embodiment, the reaction can be shown as the following scheme:

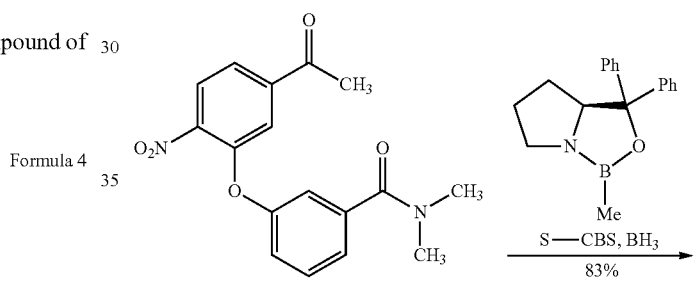

Formula 2a

S—CBS, BH₃
83%

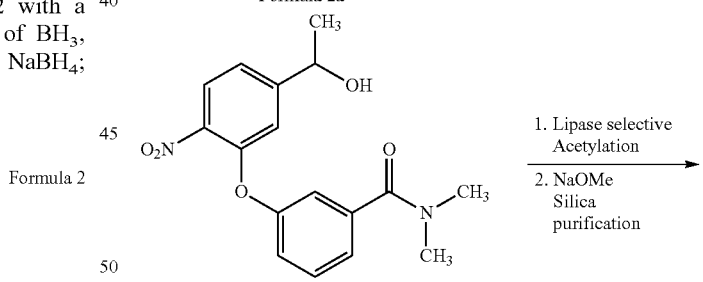

Formula 5
(R-form major)

1. Lipase selective Acetylation
2. NaOMe Silica purification

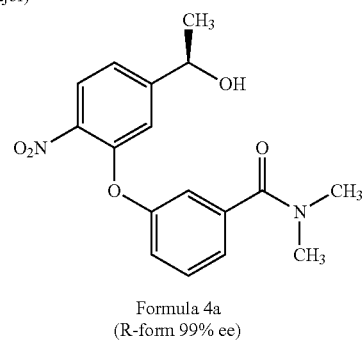

Formula 4a
(R-form 99% ee)

In an embodiment, a method for preparing a compound of Formula 4 comprises the steps:

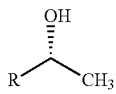

Formula 4 step (1a): reacting a compound of Formula 2 with a compound of Formula 3b in the presence of $BH_3$, DIP-Chloride, (S)-(−)-1,1'-Bi-2-naphthol, or $NaBH_4$;

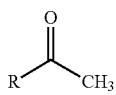

Formula 2

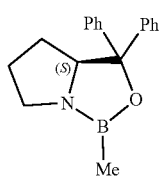

Formula 3b step (1b): reacting a product of step (1a) with acetic anhydride ($Ac_2O$); and step (2): reacting a product of step (1b) with:
(A) lipase acrylic resin, and $Na_2CO_3$; or
(B) protease, and $Na_2CO_3$; and reacting a product of step (B) with sodium methoxide in the presence of methanol wherein R is

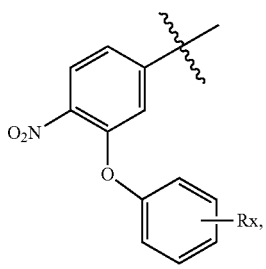

an aliphatic chain, or Rx;

wherein Rx is hydrogen, an unsubstituted or substituted cyclic ring group, an electron withdrawing group, or an electron donating group.

In an embodiment, the reaction can be shown as the following scheme:

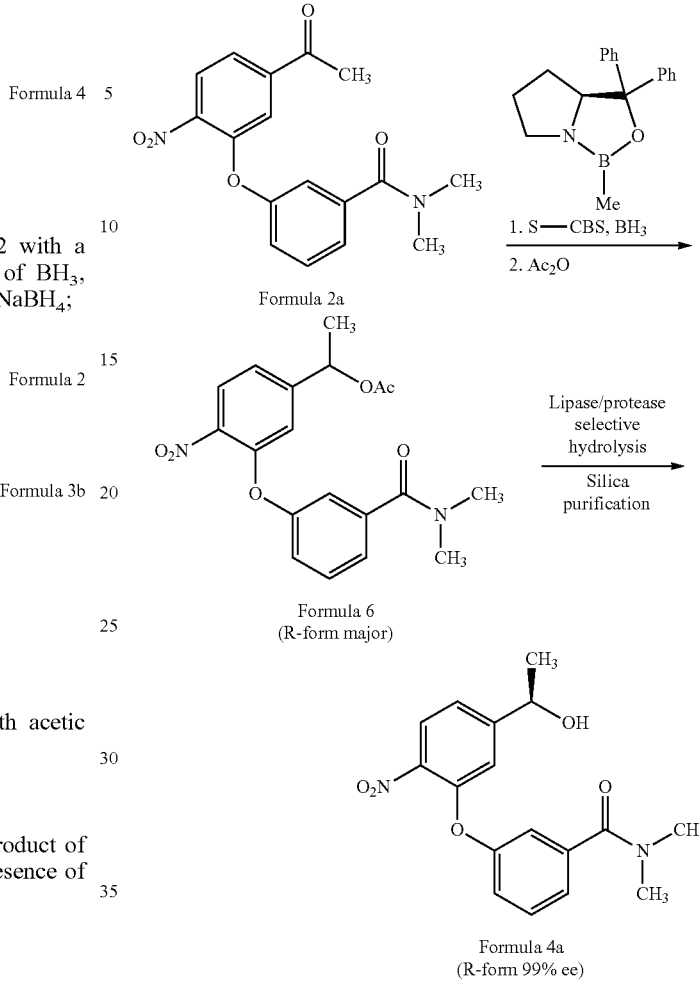

Formula 2a

Formula 6 (R-form major)

Formula 4a (R-form 99% ee)

In an embodiment, the aliphatic chain has the number of $C_6$ to $C_{20}$.

In an embodiment, the cyclic ring group is an aromatic group, a cyclic saturated or partially unsaturated group, or a heterocyclic ring group. Preferably, the heterocyclic ring group includes heteroatoms of N, O, or S.

In an embodiment, the electron withdrawing group is a halo (F, Cl, Br, I), nitroso (—N=O), aminocarbonyl (—$CONH_2$; —CONHR; —$CONR_2$, wherein R=alkyl), carboxyl (—$CO_2H$), alkoxycarbonyl (—$CO_2R$, wherein R=alkyl), formyl (—CHO), acyl (—COR, wherein R=alkyl), haloformyl (—COX, wherein X=Cl, Br, I), trihalomethyl (—$CX_3$, wherein X=F, Cl, Br, I), cyano (—C≡N), nitro (—$NO_2$), ammonium group (—$NR_3^+$, wherein R=alkyl or H), azide (—$N^-_3$), or sulfonyl group (—$SO_2R$, wherein R=H, $CF_3$, alkyl). Preferably, the alkyl group is $C_1$-$C_5$ alkyl group.

In an embodiment, the electron donating group is a low alkyl (e.g., —$CH_3$, —$C_2H_5$), vinyl (—CH=$CH_2$), phenyl (—$C_6H_5$), acyloxyl (—OCOR, wherein R=alkyl), acylamido (—NHCOR, wherein R=alkyl), alkylthio (—SR, wherein R=alkyl), sulfhyfryl (—SH), hydroxyl (—OH), alkoxy (—OR, wherein R=alkyl), amino group (—$NH_2$; —NHR; —$NR_2$, wherein R=alkyl). Preferably, the alkyl group is $C_1$-$C_5$ alkyl group.

In an embodiment, compound OBI-3424 (S-form) was successfully synthesized with 54% yield (from compound OBI-3424-5) and 99% optical purity via the two steps combination of Corey-Bakshi-Shibata (CBS) asymmetric reduction and lipase esterification. The stereo chemistry was established by two steps chemo-enzyme combination of CBS reduction and application of lipase to give at least 99% optical purity (FIG. 1).

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

The clinical trial batch of compound OBI-3424 was first synthesized by "Asymchem" with 19% yield over three steps (see Scheme 1 below). In order to improve the yield and reduce the possible impurities, the inventors tried to design another synthetic pathway (see Scheme 2), and two major approaches have been selected to accomplish the goal. First, the labile phosphate motif is introduced at the later stage and the aziridine formation in final step to avoid the nucleophile destruction of m-benzoic derivative. The synthetic route is first confirmed through racemic compound OBI-3424-6, which is prepared by using NaBH$_4$ as reductant, and then the phosphorylation and aziridine formation are proceeded in further steps. Secondly, for improvement of stereo selectivity, the stereo center is designed to be established by combination of CBS asymmetric reduction and lipase selective protection enrichment (see Scheme 3). The combination of these methods is expected to give highly optical pure product with good yield. Hence, the present invention developed alternative synthetic route to obtain the compound OBI-3424. The CBS reagent is replaced with its enantiomer for preparation of S-form majored compound OBI-3424-6 mixture. The minor amount of R-form compound OBI-3424-6 can be selectively acetylated by treatment of lipase. Then, pure S-form compound OBI-3424-6 can be obtained through column purification.

Scheme 1. The GMP synthesis process of compound OBI-3424 (clinical)

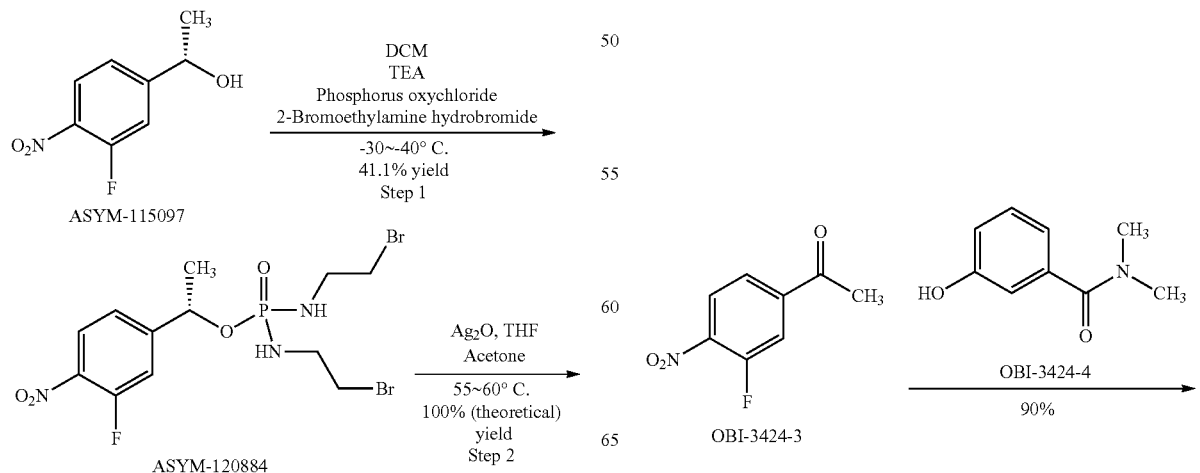

-continued

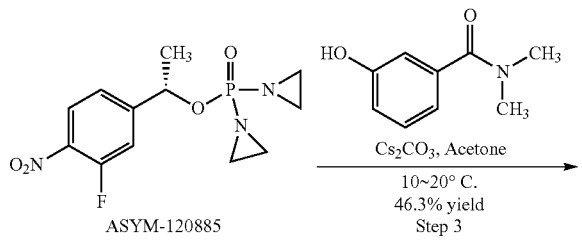

Scheme 2. New route design of compound OBI-3424 synthesis.

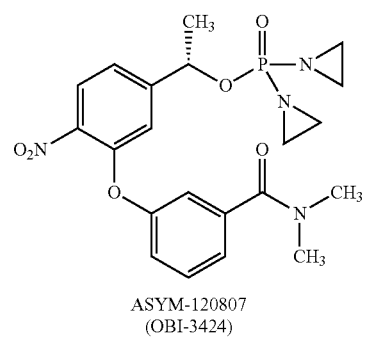

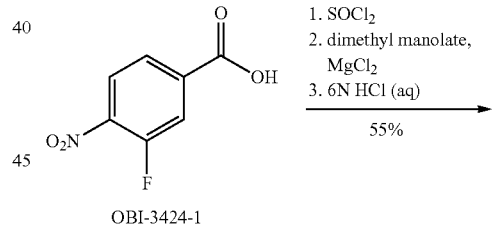

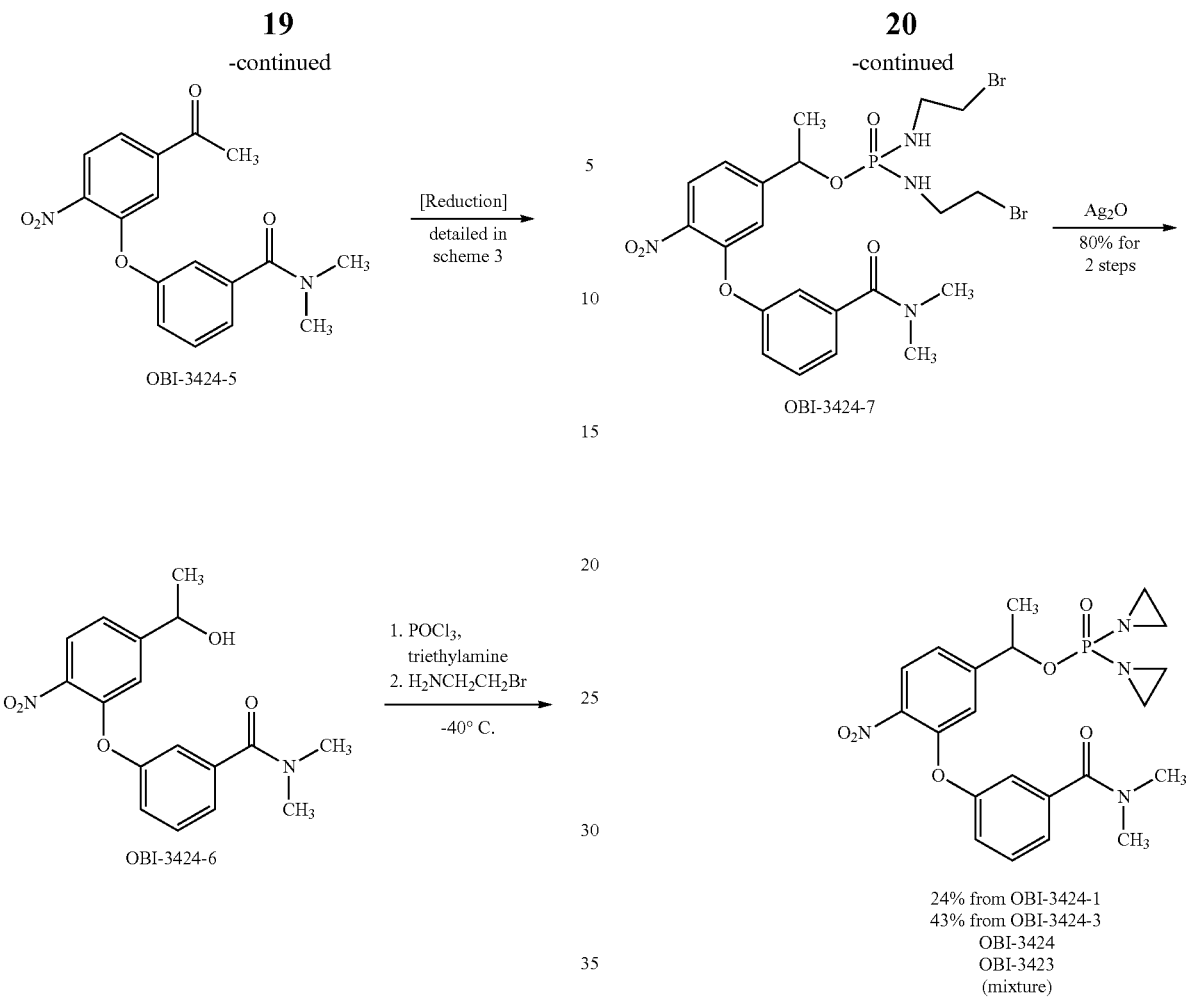
Scheme 3. Construction of stereo chemistry of compound OBI-3424-6.
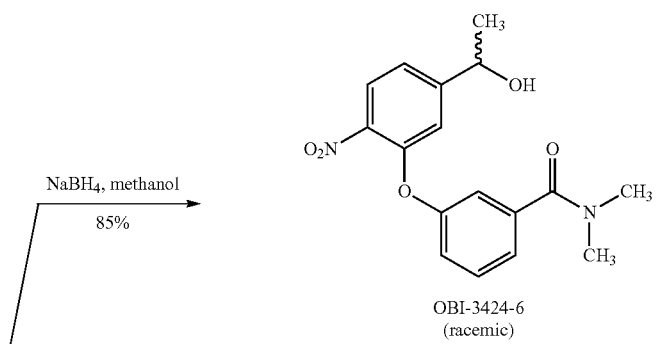

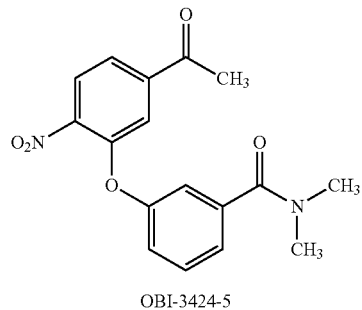

OBI-3424-5

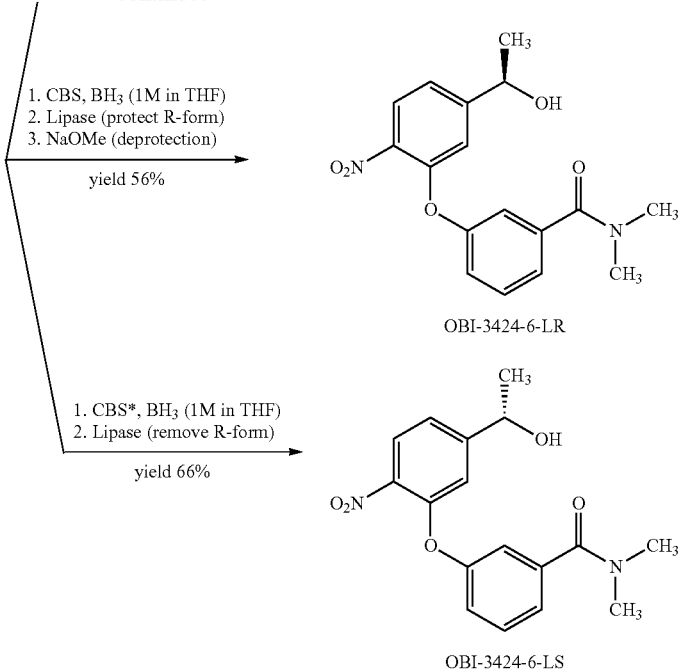

1. CBS, BH₃ (1M in THF)
2. Lipase (protect R-form)
3. NaOMe (deprotection)

yield 56%

OBI-3424-6-LR

1. CBS*, BH₃ (1M in THF)
2. Lipase (remove R-form)

yield 66%

OBI-3424-6-LS

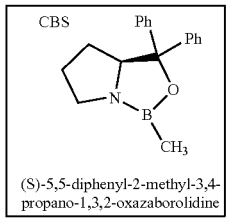

(S)-5,5-diphenyl-2-methyl-3,4-propano-1,3,2-oxazaborolidine

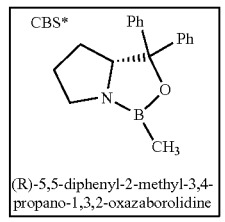

(R)-5,5-diphenyl-2-methyl-3,4-propano-1,3,2-oxazaborolidine

Materials and Methods

Equipment is listed in Table 2.

TABLE 2

| Equipment List | | | |
|---|---|---|---|
| Equipment | Manufacturer | S/N | Model/Type |
| Hotplate | IKA | N/A | RCT B S1 |
| Rotavapor | Buchi | 1000060922 | R-210 |
| Vacuum controller | Buchi | 1000064866 | V-850 |
| Heating Bath | Buchi | 1000131345 | B-491 |

TABLE 2-continued

| Equipment List | | | |
|---|---|---|---|
| Equipment | Manufacturer | S/N | Model/Type |
| Vacuum pump | Buchi | 1000052997 | V-700 |
| Vacuum pump | Buchi | 1000135289 | V-710 |
| Cooler | Panchum Scientific Corp. | 8503098 | UR-8500 |
| Cooler | HCS | 881826 | 820 |

The reagents for chemical syntheses of Scheme 2 and Scheme 3 is listed in Table 3.

TABLE 3

| Reagent List | | | | |
|---|---|---|---|---|
| Intermediate/Product | Reagent | M.W. | Equivalent | Amount |
| OBI-3424-3 | OBI-3424-1 | 185.11 | 1.00 | 12.0 g |
| | SOCl₂ | 118.97 | 8.00 | 35.0 mL |
| | DMF | 73.09 | 0.16 | 0.8 mL |
| | MgCl₂ (anhydrous) | 95.21 | 0.60 | 3.7 g |
| | Dimethyl malonate | 132.11 | 1.03 | 7.6 mL |
| | Triethylamine | 101.19 | 2.09 | 18.8 mL |
| | 6N HCl | N/A | excess | 60 mL |
| | toluene | 92.14 | ca.3M (based on OBI-3424-1) | 20 mL |
| OBI-3424-4 | m-hydroxybenzoic acid | 138.12 | 1.00 | 10.0 g |
| | Isobutyl chloroformate | 136.58 | 2.20 | 20.7 mL |
| | Triethylamine | 101.19 | 4.40 | 44.4 mL |

TABLE 3-continued

Reagent List

| Intermediate/Product | Reagent | M.W. | Equivalent | Amount |
|---|---|---|---|---|
| | Dimethylamine (2M in THF) | 45.09 | 5.00 | 181 mL |
| | THF (anhydrous) | 72.11 | ca.0.3M (based on MHBA) | 250 mL |
| OBI-3424-5 | OBI-3424-3 | 183.14 | 1.30 | 0.35 g |
| | OBI-3424-4 | 165.19 | 1.00 | 0.25 g |
| | $Cs_2CO_3$ | 325.82 | 1.80 | 0.84 g |
| | THF (anhydrous) | 72.11 | ca.0.40M (based on OBI-3424-4) | 4 mL |
| OBI-3424-6 (racemic) | OBI-3424-5 | 328 | 1.00 | 0.50 g |
| | $NaBH_4$ | 37.83 | 1.10 | 57.93 mg |
| | methanol | 32.04 | ca.0.20M (based on OBI-3424-5) | 8 mL |
| OBI-3424-6 R/S mixture | OBI-3424-5 | 328 | 1.00 | 0.45 g |
| | CBS reagent* | 277 | 0.20 | 76.00 mg |
| | $BH_3$ (1M in THF) | 85.94 | 1.05 | 1.44 mL |
| | THF (anhydrous) | 72.11 | ca.0.40M (based on OBI-3424-5) | 2 mL |
| OBI-3424-6-LR Lipase R-form (LR) selection | OBI-3424-6 R/S mixture | 330 | — | 610 mg |
| | Isopropenyl acetate | 102 | — | 5063 µL |
| | $Na_2CO_3$ | 106 | — | 61 mg |
| | Lipase (CALB, Sigma Cat#: L4777) | — | ≥5000 U/g | 460 mg |
| | NaOMe | 54.02 | 0.2 | 20 mg |
| OBI-3424-6-LS Lipase S-form (LS) selection | OBI-3424-6 R/S mixture | 330 | — | 150 mg |
| | Isopropenyl acetate | 102 | — | 2000 µL |
| | $Na_2CO_3$ | 106 | — | 5 mg |
| | Lipase (CALB, Sigma Cat#: L4777) | — | ≥5000 U/g | 150 mg |

NOTE*:
Two CBS reagents were used to prepare compound OBI-3424-6 R/S mixture: (S)-5,5-diphenyl-2-methyl-3,4-propano-1,3,2-oxazaborolidine (CAS = [112022-81-8]) would afford R-form majored product, while (R)-5,5-diphenyl-2-methyl-3,4-propano-1,3,2-oxazaborolidine (CAS = [112022-83-0]) would give S-form majored product.

Experimental Substrates

Substrate 1: 1-(3-(3-N,N-dimethylaminocarbonyl)phenoxyl-4-nitrophenyl)ethanol $^1$H NMR (400 MHz, $CDCl_3$) δ 7.97 (d, J=0.4 Hz, 1H), 7.41 (t, J=8.0 Hz, 1H), 7.26-7.19 (m, 2H), 7.11-7.09 (m, 2H), 7.03 (d, J=1.2 Hz, 1H), 4.88 (q, J=6.4 Hz, 1H), 3.08 (s, 3H), 2.97 (s, 3H), 1.44 (d, J=6.4 Hz, 3H) ppm; $^{13}$C NMR (100 MHz, $CDCl_3$) δ 170.5 (C), 156.2 (C), 154.0 (C), 150.0 (C), 140.2 (C), 138.0 (C), 130.2 (CH), 126.0 (CH), 122.6 (CH), 120.8 (CH), 119.9 (CH), 118.2 (CH), 117.1 (CH), 68.9 (CH), 39.5 ($CH_3$), 35.3 ($CH_3$), 25.2 ($CH_3$) ppm; HRMS (ESI, M+Na$^+$) calcd for $C_{17}H_{18}N_2O_5Na$ 353.1108, found 353.1108.

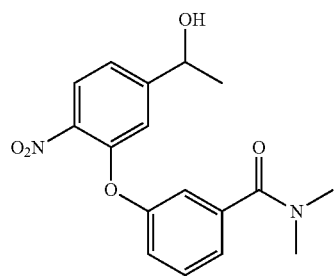

Substrate 1

Substrate 2: 1-(3-fluoro-4-nitrophenyl)ethan-1-ol $^1$H NMR (400 MHz, $CDCl_3$) δ 8.00 (t, J=8.0 Hz, 1H), 7.34 (dd, J=12.0, 1.6 Hz, 1H), 7.29-7.27 (m, 1H), 4.99 (q, J=6.8 Hz, 1H), 2.49 (s, 1H), 1.51 (d, J=6.8 Hz, 3H) ppm; $^{13}$C NMR (100 MHz, $CDCl_3$) δ 157.0 (C), 155.3 (C), 155.2 (C), 154.4 (C), 126.2 (CH), 121.2 (CH), 115.2 (CH), 114.9 (CH), 68.9 (CH), 25.3 ($CH_3$) ppm; HRMS (ESI, M+Na$^+$) calcd for $C_8H_8FNO_3Na$ 208.0380, found 208.0354.

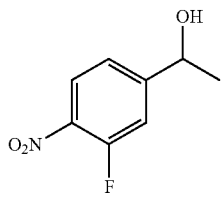

Substrate 2

Substrate 3: 1-(3-(4-(trifluoromethyl)phenoxyl)-4-nitrophenyl)ethan-1-ol $^1$H NMR (400 MHz, $CDCl_3$) δ 8.01 (d, J=8.4 Hz, 1H), 7.62 (d, J=8.8 Hz, 2H), 7.31 (dd, J=8.0, 1.2 Hz, 1H), 7.18 (d, J=2.0 Hz, 1H), 7.07 (d, J=8.4 Hz, 2H), 4.95 (q, J=6.4 Hz, 1H), 2.02 (s, 1H), 1.48 (d, J=6.4 Hz, 3H) ppm; $^{13}$C NMR (100 MHz, $CDCl_3$) δ 159.2 (C), 153.7 (C), 149.0 (C), 140.7 (C), 127.43 (CH), 127.40 (CH), 126.3 (CH), 121.6 (CH), 119.1 (CH), 117.8 (CH), 69.1 (CH), 25.5 (CH$_3$) ppm; HRMS (ESI, M+Na$^+$) calcd for C$_{15}$H$_{12}$F$_3$NO$_4$Na 350.0611, found 350.0607.

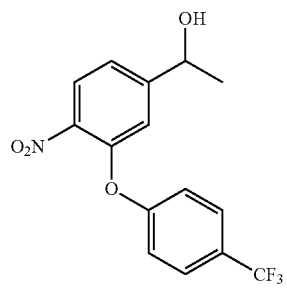

Substrate 3

Substrate 4: 1-(3-(4-(2-methylphenyl)phenoxyl)-4-nitrophenyl)ethan-1-ol $^1$H NMR (400 MHz, CDCl$_3$) δ 7.97 (d, J=8.4 Hz, 1H), 7.32 (dd, J=6.4, 2.0 Hz, 2H), 7.27-7.20 (m, 5H), 7.16 (d, J=1.6 Hz, 1H), 7.07 (dd, J=6.8, 2.0 Hz, 2H), 4.91 (q, J=6.8 Hz, 1H), 2.29 (s, 3H), 1.47 (d, J=6.4 Hz, 3H) ppm; $^{13}$C NMR (100 MHz, CDCl$_3$) δ 154.8 (C), 153.2 (C), 150.8 (C), 140.8 (C), 140.2 (C), 138.1 (C), 135.4 (C), 130.8 (CH), 130.4 (CH), 129.8 (CH), 127.4 (CH), 126.1 (CH), 125.8 (CH), 120.1 (CH), 118.4 (CH), 117.6 (CH), 69.3 (CH), 25.4 (CH$_3$), 20.5 (CH$_3$) ppm; HRMS (ESI, M+Na$^+$) calcd for C$_{21}$H$_{19}$NO$_4$Na 372.1206, found 372.1204.

Substrate 4

Substrate 5: 1-(2-chloro-4-nitrophenyl)ethan-1-ol $^1$H NMR (400 MHz, CDCl$_3$) δ 8.21 (d, J=2.4 Hz, 1H), 8.16 (dd, J=8.4, 2.4 Hz, 1H), 7.85 (d, J=8.4 Hz, 1H), 5.34 (q, J=6.4 Hz, 1H), 2.24 (s, 1H), 1.51 (d, J=6.8 Hz, 3H) ppm; $^{13}$C NMR (100 MHz, CDCl$_3$) δ 150.5 (C), 147.2 (C), 132.1 (C), 127.3 (CH), 124.6 (CH), 122.2 (CH), 66.8 (CH), 23.6 (CH$_3$) ppm; HRMS (ESI, M+Na$^+$) calcd for C$_8$H$_8$ClNO$_3$Na 224.0085, found 224.0085.

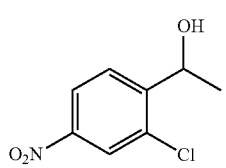

Substrate 5

Substrate 6: 1-(3-chloro-4-nitrophenyl)ethan-1-ol $^1$H NMR (400 MHz, CDCl$_3$) δ 7.87 (d, J=8.4 Hz, 1H), 7.58 (d, J=2.0 Hz, 1H), 7.40 (dd, J=8.4, 1.6 Hz, 1H), 4.97 (q, J=6.4 Hz, 1H), 2.40 (s, 1H), 1.51 (d, J=6.4 Hz, 3H) ppm; $^{13}$C NMR (100 MHz, CDCl$_3$) δ 152.1 (C), 146.5 (C), 128.7 (CH), 127.3 (C), 125.9 (CH), 124.4 (CH), 68.9 (CH), 25.4 (CH$_3$) ppm; HRMS (ESI, M+Na$^+$) calcd for C$_8$H$_8$ClNO$_3$Na 224.0085, found 224.0065.

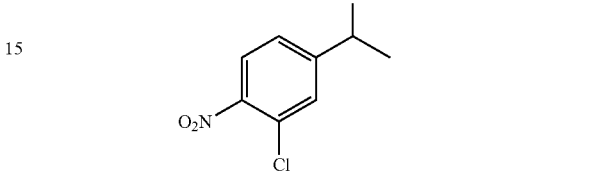

Substrate 6

Substrate 7: 1-(3-methoxy-4-nitrophenyl)ethan-1-ol $^1$H NMR (400 MHz, CDCl$_3$) δ 7.83 (d, J=8.4 Hz, 1H), 7.16 (d, J=1.6 Hz, 1H), 6.97 (dd, J=8.4, 1.6 Hz, 1H), 4.96 (q, J=6.4 Hz, 1H), 3.97 (s, 3H), 2.42 (s, 1H), 1.50 (d, J=6.4 Hz, 3H) ppm; $^{13}$C NMR (100 MHz, CDCl$_3$) δ 153.3 (C), 138.1 (C), 126.0 (CH), 117.0 (CH), 110.1 (CH), 69.5 (CH), 56.4 (CH$_3$), 25.4 (CH$_3$) ppm; HRMS (ESI, M+Na$^+$) calcd for C$_9$H$_{11}$NO$_4$Na 220.0580, found 220.0555.

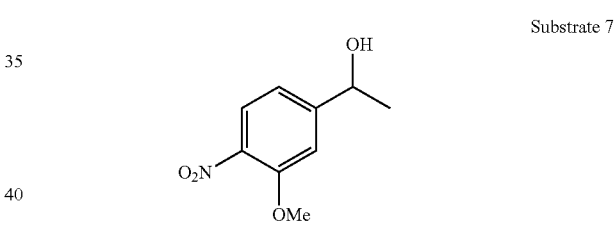

Substrate 7

Substrate 8: 1-(2-methoxy-4-nitrophenyl)ethan-1-ol $^1$H NMR (400 MHz, CDCl$_3$) δ 7.86 (dd, J=8.4, 2.0 Hz, 1H), 7.71 (d, J=2.0 Hz, 1H), 7.59 (d, J=8.4 Hz, 1H), 5.18 (q, J=6.4 Hz, 1H), 3.96 (s, 3H), 2.43 (s, 1H), 1.49 (d, J=6.4 Hz, 3H) ppm; $^{13}$C NMR (100 MHz, CDCl$_3$) δ 156.4 (C), 147.9 (C), 141.3 (C), 126.3 (CH), 116.2 (CH), 105.3 (CH), 65.5 (CH), 55.9 (CH$_3$), 23.1 (CH$_3$) ppm; HRMS (ESI, M+Na$^+$) calcd for C$_9$H$_{11}$NO$_4$Na 220.0580, found 220.0557.

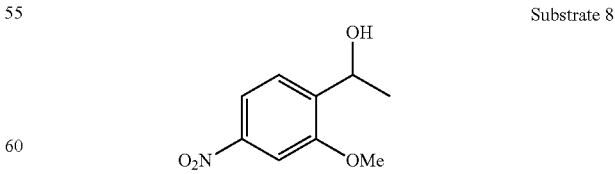

Substrate 8

Substrate 9: 1-phenylethanol $^1$H NMR (400 MHz, CDCl$_3$) δ 7.35-7.30 (m, 4H), 7.27-7.24 (m, 1H), 4.84 (q, J=6.4 Hz, 1H), 2.31 (s, 1H), 1.46 (d, J=6.4 Hz, 3H) ppm; $^{13}$C NMR (100 MHz, CDCl$_3$) δ 145.7 (C), 128.4 (CH), 127.4 (CH), 125.3 (CH), 70.3 (CH), 25.0 (CH$_3$) ppm; HRMS (ESI, M+Na$^+$) calcd for C$_8$H$_{10}$ONa 145.0624, found 145.0621.

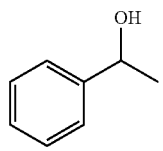

Substrate 9

Substrate 10: 2-Octanol $^1$H NMR (400 MHz, CDCl$_3$) δ 3.83-3.75 (m, 1H), 1.76 (s, 1H), 1.46-1.26 (m, 10H), 1.18 (d, J=6.0 Hz, 3H), 0.89 (t, J=6.8 Hz, 3H) ppm; $^{13}$C NMR (100 MHz, CDCl$_3$) δ 68.1 (CH), 39.3 (CH$_2$), 31.8 (CH$_2$), 29.3 (CH$_2$), 25.7 (CH$_2$), 23.4 (CH$_3$), 22.6 (CH$_2$), 14.0 (CH$_3$) ppm; HRMS (ESI, M+Na$^+$) calcd for C$_8$H$_{18}$ONa 153.1250, found 153.1237.

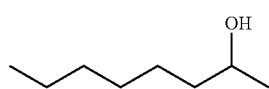

Substrate 10

Substrate 11: N-[4-(1-Hydroxyethyl)phenyl]acetamide $^1$H NMR (400 MHz, CDCl$_3$) δ 7.50 (d, J=8.4 Hz, 2H), 7.31 (d, J=8.4 Hz, 2H), 4.79 (q, J=6.4 Hz, 1H), 2.11 (s, 3H), 1.42 (d, J=6.4 Hz, 3H) ppm; $^{13}$C NMR (100 MHz, CDCl$_3$) δ 171.8 (C), 143.5 (C), 138.9 (C), 127.1 (CH), 121.2 (CH), 70.6 (CH), 25.6 (CH$_3$), 23.9 (CH$_3$) ppm; HRMS (ESI, M+Na$^+$) calcd for C$_{10}$H$_{13}$NO$_2$Na 202.0838, found 202.0809.

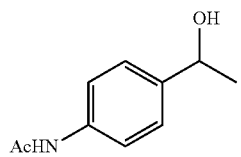

Substrate 11

Substrate 12: 1-O-acetyl-1-(3-(3-N, N-dimethylaminocarbonyl)phenoxyl-4-nitrophenyl)ethane $^1$H NMR (400 MHz, CDCl$_3$) δ 7.96 (d, J=8.4 Hz, 1H), 7.42 (td, J=7.6, 2.4 Hz, 1H), 7.24-7.20 (m, 2H), 7.09-7.04 (m, 3H), 5.78 (q, J=6.8 Hz, 1H), 3.10 (s, 3H), 2.98 (s, 3H), 2.06 (s, 3H), 1.48 (d, J=6.8 Hz, 3H) ppm; $^{13}$C NMR (100 MHz, CDCl$_3$) δ 170.3 (C), 169.9 (C), 155.9 (C), 150.0 (C), 149.4 (C), 140.6 (C), 138.4 (C), 130.2 (CH), 126.2 (CH), 122.8 (CH), 121.2 (CH), 119.6 (CH), 118.7 (CH), 117.1 (CH), 70.9 (CH), 39.5 (CH$_3$), 35.3 (CH$_3$), 22.1 (CH$_3$), 21.2 (CH$_3$) ppm; HRMS (ESI, M+Na$^+$) calcd for C$_{19}$H$_{20}$N$_2$O$_6$Na 395.1214, found 395.1146.

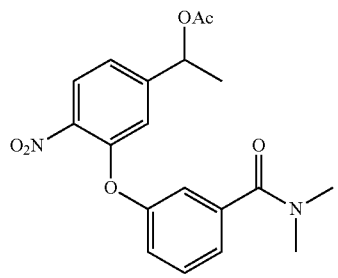

Substrate 12

Substrate 13: 1-O-acetyl-1-(3-fluoro-4-nitrophenyl)ethane $^1$H NMR (400 MHz, CDCl$_3$) δ 8.06 (dd, J=8.4, 7.2 Hz, 1H), 7.30-7.25 (m, 2H), 5.87 (q, J=6.8 Hz, 1H), 2.13 (s, 3H), 1.55 (d, J=6.8 Hz, 3H) ppm; $^{13}$C NMR (100 MHz, CDCl$_3$) δ 169.9 (C), 157.0 (C), 154.3 (C), 150.9 (C), 150.8 (C), 126.5 (CH), 121.82 (CH), 121.79 (CH), 115.8 (CH), 115.6 (CH), 70.6 (CH), 22.1 (CH$_3$), 21.0 (CH$_3$) ppm; HRMS (ESI, M+Na$^+$) calcd for C$_{10}$H$_{10}$FNO$_4$Na 250.0486, found 250.0445.

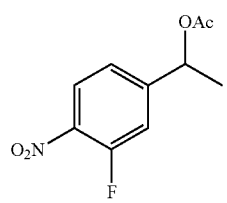

Substrate 13

Example 1: Synthesis of Compound OBI-3424 Intermediates (from Compound OBI-3424-3 to Compound OBI-3424-5)

Synthesis of OBI-3424-3

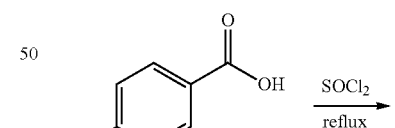

OBI-3424-1

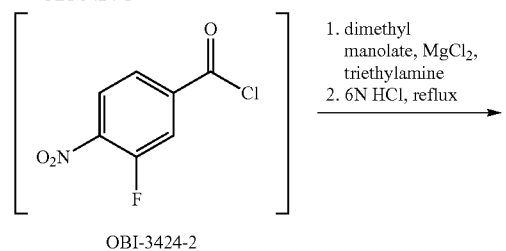

OBI-3424-2

-continued

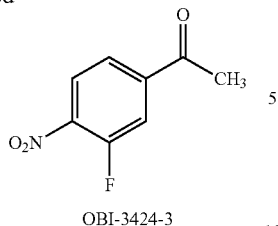

OBI-3424-3

In a round-bottom flask, a mixture of compound OBI-3424-1 (9 g, 48.6 mmol), dimethyl formamide (0.1 g, mmol) and thionyl chloride (SOCl$_2$, 30 mL, mmol) was refluxed at 75° C. for 3 hours. During the refluxing, mixed anhydrous MgCl$_2$ (2.79 g, mmol), dimethyl malonate (5.7 mL, mmol) and triethyl amine (14.1 mL, mmol) in another round-buttoned flask at room temperature (ca. 25° C.). The resulted white suspension was stirred for 1.5 h and turned into white mud. After refluxing for 3 hours, the reaction mixture of compound OBI-3424-1 and SOCl$_2$ was then cooled to around 40° C. The reaction mixture was then concentrated by a rotatory evaporator to remove excess solvents. The resulted syrup was then diluted with 15 mL toluene. The resulted toluene solution was added drop wise into the white mud mixture prepared in advance. After mixing for 1.5 hours, check the reaction by TLC (volume ratio EtOAc/n-hexane=1:4). The resulted mixture was treated with 30 mL 6N HCl, and then extracted with 60 mL EtOAc. The aqueous layer was extracted with 60 mL EtOAc again. The combined organic layer was dried over MgSO$_4$, filtered and then concentrated by the rotatory evaporator (temperature of water bath=ca. 35° C., pressure=ca. 130 mbar) to afford a reddish syrup. The resulted syrup was mixed with 30 mL 6N HCl, and then reflux at 100° C. for ca. 17 hours. After then, the resulted reaction crude was cooled to room temperature, diluted with 60 mL EtOAc, and extracted. The aqueous layer was extracted with 60 mL EtOAc again. The organic layer was collected, dried over MgSO$_4$, filtered, and then concentrated by the rotatory evaporator (temperature of water bath=ca. 35° C., pressure=ca. 130 mbar) to afford a reddish syrup. The resulted syrup was purified by column chromatography through a pad of silica gel (200 g gel powder for 10 g compound OBI-3424-1). The column was packed with silica gel mixed volume ratio hexane/EtOAc/CH$_2$Cl$_2$=12/1/0.5; the eluent system was suggested as hexane/EtOAc/CH$_2$Cl$_2$=12/1/0.5 (1 column volume), 10/1/1 (2-3 column volume). The collected product was concentrated by the rotatory evaporator (temperature of water bath=ca. 35° C., pressure=ca. 130 mbar) and high vacuum (ca. 25° C., about 17 hours) to afford expected product compound OBI-3424-3 as yellow solid (5.4 g, 55% isolated yield).

Synthesis of Compound OBI-3424-4

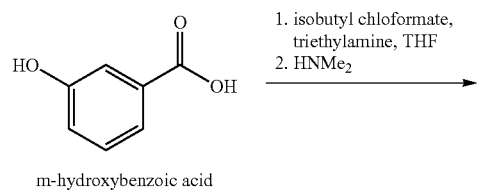

m-hydroxybenzoic acid

-continued

OBI-3424-4

Dissolved m-hydroxybenzoic acid (15 g) in THF (anhydrous, 300 mL) and then cooled the reaction to −30° C. under nitrogen protection. After 20 min. stirring, added triethylamine (67 mL) into the chilled reaction over 15 min. After 15 min. stirring, the reaction became a white suspension. Added isobutyl chloroformate (31 mL) into the resulted suspension over 15 min. After stirring for 2 hours, checked TLC (volume ratio CH$_2$Cl$_2$/EtOAc=2/1). Upon the m-hydroxybenzoic acid ceased, dimethylamine (2 M in THF, 270 mL) was added into the reaction over 30 min. The reaction was stirred for another 30 min. after addition, and then warmed to room temperature (ca. 25° C.) for continuous 18 hours stirring. Upon reaction completed, water (90 mL) was added into the reaction, and then THF was removed by the rotatory evaporator (temperature of water bath=35° C., ca. 100 mbar). After then, the reaction crude was extracted using chilled 1N HCl (30 mL) and EtOAc (200 mL). The aqueous layer was extracted with EtOAc (200 mL) twice. The organic extracts were combined, dried over MgSO$_4$, filtered, and then concentrated to ca. 30% volume by the rotatory evaporator with some crystal participated out (temperature of water bath=35° C., ca. 120 mbar). The resulted crude sample was then treated with hexane (200 mL) with stirring (360 rpm) to form a white suspension. The resulted solid was filtered, washed with chilled volume ratio hexane/EtOAc mixture=20/1, dried by high-vacuum system for ca. 16 hours (25° C.) to afford the expected compound OBI-3424-4 as white solid (12.7 g, 71% isolated yield).

Synthesis of Compound OBI-3424-5

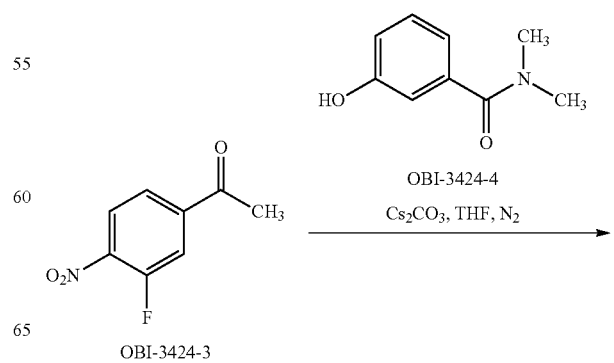

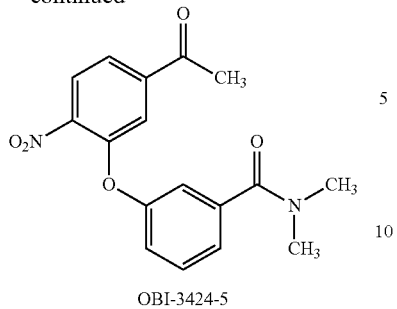

OBI-3424-5

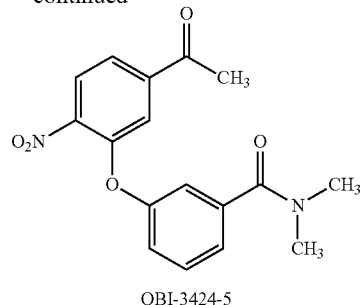

OBI-3424-5

Compound OBI-3424-3 (0.35 g) was added into an anhydrous THF solution (4 mL) of compound OBI-3424-4 (0.25 g) in a proper two-necked round bottomed bottle at room temperature (=ca. 23° C.) under nitrogen protection. The reaction mixture was chilled to 0° C. for 15 min. $Cs_2CO_3$ (0.84 g) was added into the chilled reaction. After 1 hour of addition, check TLC (volume ratio $CH_2Cl_2$/EtOAc=2/1, Rf value of compound OBI-3424-5=0.3). Upon compound OBI-3424-4 ceased, the reaction was diluted with 8 mL EtOAc, and extracted with 4 mL sat. $NH_4C$. The aqueous layer was extracted with 8 mL EtOAc twice. The organic layer was combined, washed with 4 mL of brine, dried over $MgSO_4$, and then concentrated by the rotatory evaporator (water bath=ca. 35° C., ca. 130 mbar) to afford a yellow syrup. The syrup was purified by column chromatography through a silica gel pad. The eluent system was suggested as described below: (volume ratio packing=Hexane/EtOAc=5/1) Hexane/EtOAc=4/1 (1 column volume), Hexane/EtOAc=1/1 (1 column volume), Hexane/EtOAc=1/2 (3 column volume) till expected product was collected. Fractions were concentrated by the rotatory evaporator (water bath=ca. 35° C., ca. 140 mbar) and high-vacuum (ca. 25° C. 16 hours) to afford compound OBI-3424-5 as light-yellow solid (0.46 g, 93% isolated yield).

The inventors first successfully synthesized compound OBI-3424-3 and compound OBI-3424-4 with acceptable yield from literature recorded method (PCT patent publication WO 2016/145092A1). After then, compound OBI-3424-5 was prepared from coupling of compound OBI-3424-3 and compound OBI-3424-4 with ca. 80% yield under the treatment of basic condition. Due to the operational convenience and to improve yield, the inventors then tested several conditions. After several tests, anhydrous THF and $Cs_2CO_3$ afforded the highest yield (Table 4). The condition using THF as reaction solvent and $Cs_2CO_3$ as base afford the best isolated yield. Furthermore, $Cs_2CO_3$ is generally considered as an operational convenience mild base, which may operationally benefit in mass production.

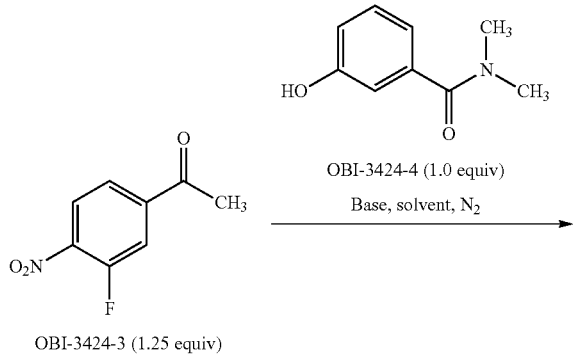

OBI-3424-3 (1.25 equiv)

OBI-3424-4 (1.0 equiv)

Base, solvent, $N_2$

TABLE 4

Condition improvement of preparation of OBI-3424-5

| Trial | Base (1.7 equiv.) | Solvent | Isolated yield |
| --- | --- | --- | --- |
| 1 | Sodium hydride | DMF | 80% |
| 2 | Sodium hydride | $CH_3CN$ | 83% |
| 3 | Sodium hydride | THF | 78% |
| 4 | $Cs_2CO_3$ | DMF | 80% |
| 5 | $Cs_2CO_3$ | $CH_3CN$ | 82% |
| 6 | $Cs_2CO_3$ | THF | 93% |

Note:
All solvents were anhydrous (commercial) and directly used without further treatment.

Example 2: Synthesis of Compound OBI-3424-6 (Racemic) Form Compound OBI-3424-5

Scheme 4. Synthesis of compound OBI-3424-6 (racemic) from compound OBI-3424-5

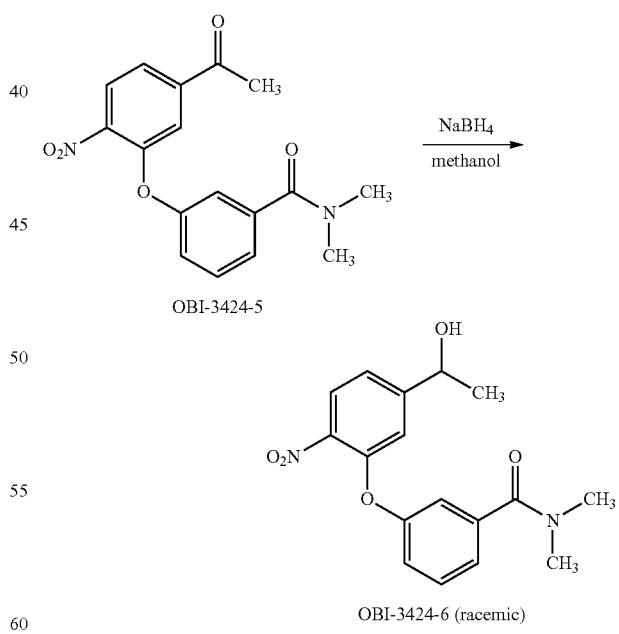

OBI-3424-5

OBI-3424-6 (racemic)

To prove the designed route works or not (see Scheme 2), compound OBI-3424-5 was soon reduced by $NaBH_4$ to obtain compound OBI-3424-6 (racemic) with 85% isolated yield (see Scheme 4). The reaction was proceeded smoothly under ice-bathe. Notice that hydrogen gas would release after addition of $NaBH_4$. The resulted compound OBI- 3424-6 (racemic) was used for next steps for exploration of synthesis of compound OBI-3424.

Compound OBI-3424-5 (500 mg) was dissolved in methanol and then chilled to 0° C. Sodium borohydride ($NaBH_4$, 58 mg) was added into this solution (NOTICE: gas would release during reaction). After stirring for 30 min, check TLC. (volume ratio $CH_2Cl_2$/EtOAc=2/1, Rf value of compound OBI-3424-5=0.3, Rf value of compound OBI-3424-6=0.2). Upon the reaction completed, the reaction was diluted with EtOAc (50 mL) and 1N HCl (5 mL). The resulted crude was separated. The aqueous layer was extracted with EtOAc again. The organic layer was collected, dried over $MgSO_4$, filtered, and then concentrated by the rotatory evaporator to afford a syrup (temperature of water bath=35° C., ca. 70 mbar). The resulted syrup was then purified through column chromatography via a silica gel pad (silica gel=20 g). The eluent system was suggested as described below: (volume ratio packing=Hexane/EtOAc=3/1), eluent: Hexane/EtOAc=1/1 (1 column volume), $CH_2Cl_2$/EtOAc=2/1 (1 column volume), $CH_2Cl_2$/EtOAc=1/1 (3 column volume) till the expected product was collected. The collected product was concentrated by the rotatory evaporator (water bath=35° C., ca. 120 mbar) and high-vacuum (ca. 25° C., 16 hours) to afford compound OBI-3424-6 (racemic) as a yellow syrup (428 mg, 85% isolated yield).

Example 3: Synthesis of Compound OBI-3424-6-LR

In 1981, S. Itsuno were the first to report this method. Several years later, E. J. Corey showed that modified catalyst was found rapid and high enantioselective reduction of achiral ketones in the presence of $BH_3$/THF. The catalytic oxazaborolidine is called Corey-Bakshi-Shibata (CBS) reduction. This catalyst was applied in many substrates and have good enantioselective (J. Mol. Catal. B Enz. 1997, 3: 65-72). According to the published results, the similar substrate will prefer to form the R-form product by using S-CBS catalyst. Hence, the inventors tried S-CBS in substrate (compound OBI-3424-5), and found the selectivity was approximately volume ratio 3:1 to 6:1 R/S ratio. To enhance the enantiomeric excess, ee %, of R-form product, the inventors then combined the lipase selective acetylation to improve the R/S ratio (see Scheme 2). The lipase selective acetylation of achiral alcohol is a mature technology. Based on published result, lipase will prefer to react with R form substrate. Two different lipases, CAL-B and PAL, have been tested and the CAL-B showed the better results. The ee % of final product of compound OBI-3424-6 can be improved to no less than 97% in HPLC after combination of S-CBS reduction and lipase acetylation.

Step 1. S-CBS Asymmetric Reduction (R Form Major)

Figure 2:
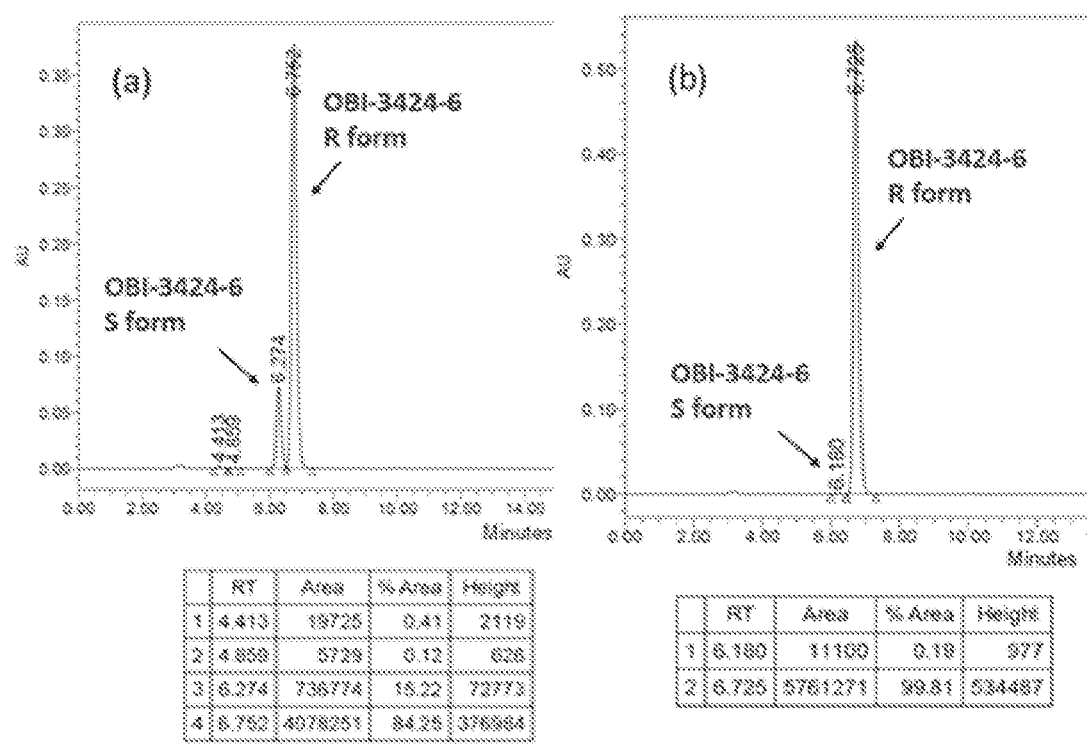
FIG. 2. The chiral HPLC data of compound OBI-3424-6: (a) OBI-3424-6 R/S mixture after CBS reduction, R/S=84.25/15.22 (69.4% ee), (b) compound OBI-3424-6-FR after lipase enrichment (99.8% ee).

After then, we focused at asymmetric reduction and improvement of optical purity. The commercial CBS reagent ((S)-5,5-diphenyl-2-methyl-3,4-propano-1,3,2-oxazaborolidine, CAS=[112022-81-8]) is known been developed from Prof. E. J. Corey (J. Am. Chem. Soc. 1987, 109: 7925-7926). This reagent can perform a chiral reduction with ketone to afford good yield of R form alcohol and high stereo selectivity with $BH_3$ in THF. Compound OBI-3435-5 was treated with 0.2 mol. equivalent of CBS reagent and 1.05 mol. equivalent of borane (1 M in THF) to give the reduced product (compound OBI-3424-6 enantiomer mixture) with 80% yield under nitrogen protection in couple hours. The optical resolution was 48% judged by chiral HPLC analysis (FIG. 2). The optical purity could be improved to 70% ee by increased the amount of CBS to 0.5 mol. equiv. and lower the reaction temperature to −20° C. But the yield would decrease to 65%, and the reaction time would increase to 22 hours (Table 5).

TABLE 5

| | The trials of CBS reduction (R form major) | | | |
|---|---|---|---|---|
| Trial | CBS reagent (equiv.) | Reaction Temperature (° C.) | Enantiomer ratio (R/S) | Isolated yield (%) |
| 1 | 0.2 | 0 to 25 | 74/26 | 48 |
| 2 | 0.5 | −20 | 85/15 | 65 |

Step 2. Lipase Selective Acyl Protection

Lipase with high R-form selectivity is an excellent enzyme for separation of compound OBI-3424-6 R/S mixture, which actively adds acetyl group to R-form compound OBI-3424-6 and passively leaves non-acetylated S-form compound OBI-3424-6 (see Scheme 5). This enantiomer mixture was then treated with lipase to selectively esterify the hydroxyl group of R-form enantiomer. The optical purity of resulted acetylated product "compound OBI-3424-6-Ac" could be enriched to 99% ee value. The acetyl group of compound OBI-3424-6-Ac was then removed under a mild basic condition to afford homemade compound OBI-3424-6-LR, and successfully converted to "compound OBI-3424-LR" with 77% isolated yield.

Scheme 5. The preparation of compound OBI-3424-6-LR through combination of CBS reduction and lipase enrichment.

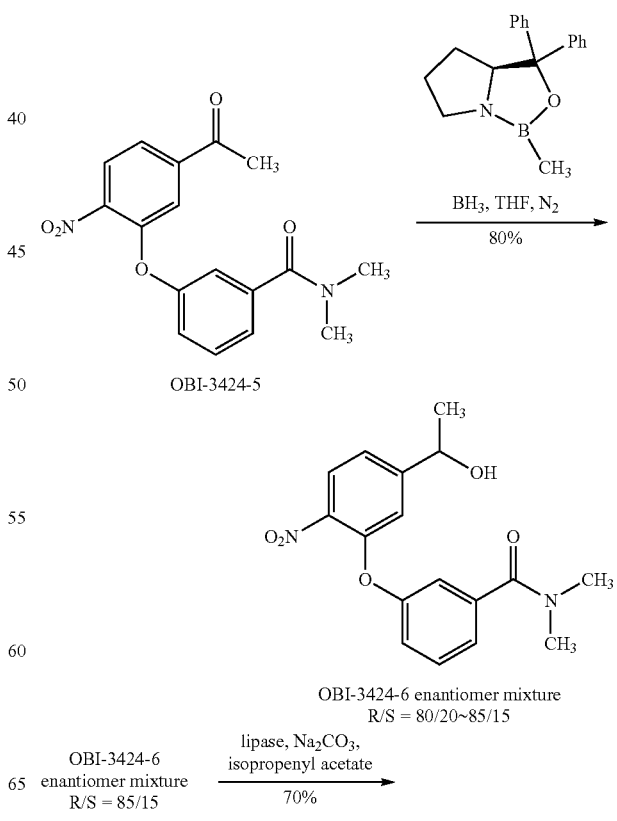

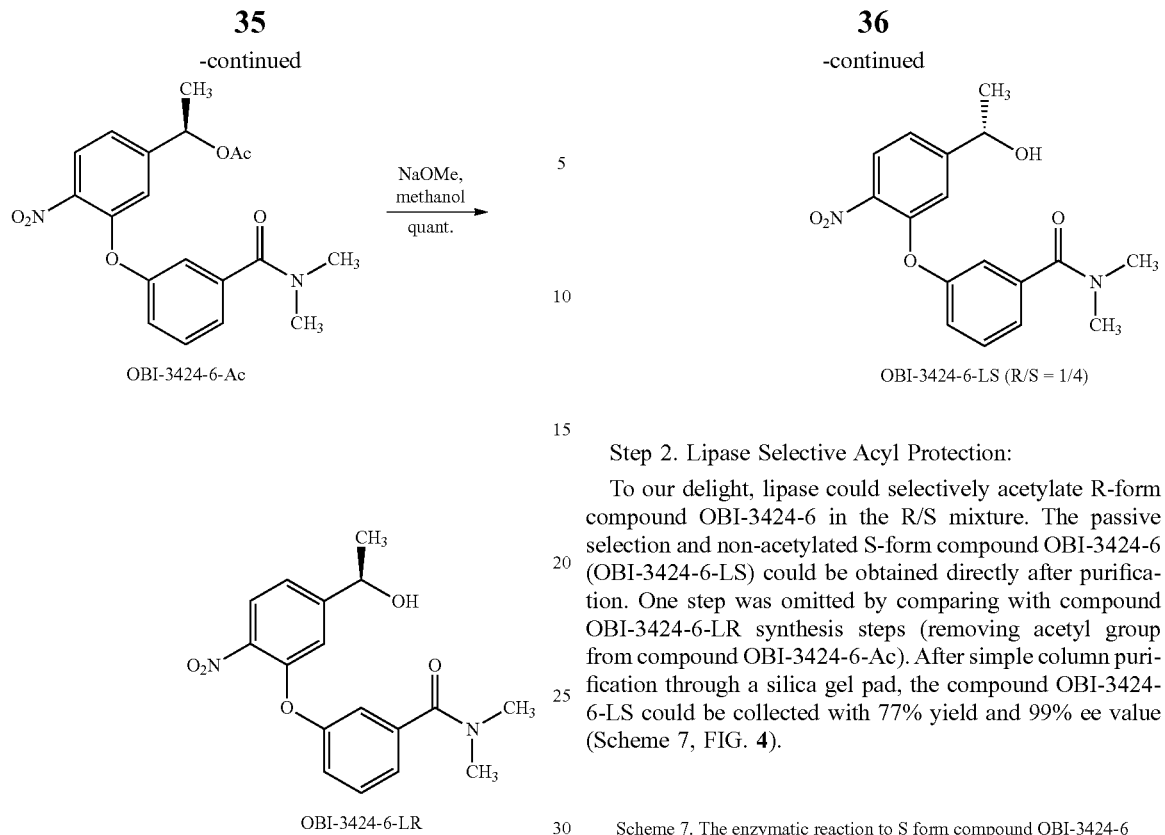

Example 4: Synthesis of Compound OBI-3424-6-LS

Figure 3:
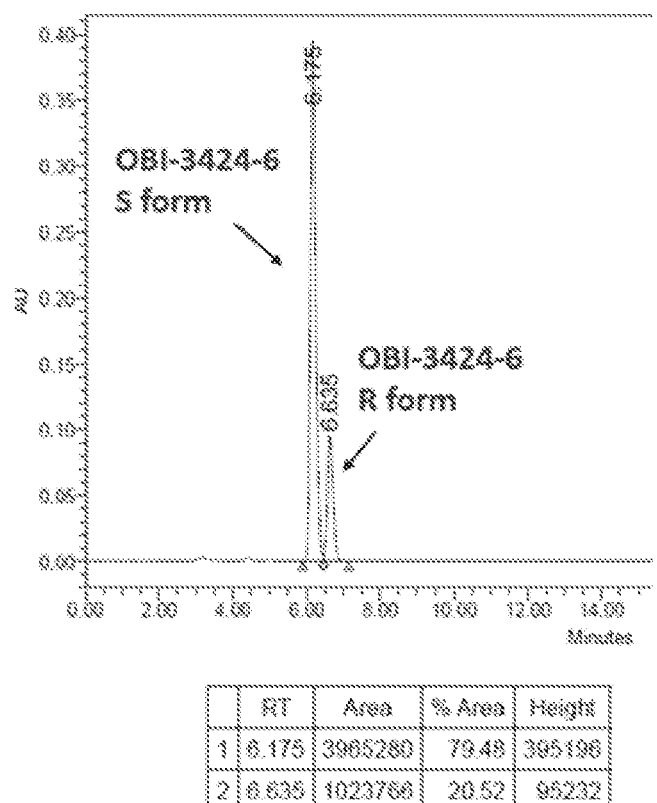
FIG. 3. The chiral HPLC data of S-form majored compound OBI-3424-6 by asymmetric reduction using (R)-CBS and BH$_3$ in THF.

Step 1. R-CBS Asymmetric Reduction (S Form Major):

After structure confirmation, the inventors then modified the synthesis pathway to produce compound OBI-3424-6 (see Scheme 6). The CBS reagent was replaced as (R)-5,5-diphenyl-2-methyl-3,4-propano-1,3,2-oxazaborolidine (CAS=[112022-83-0]). The asymmetric reduction of compound OBI-3424-5 afforded compound OBI-3424-6 enantiomer mixture with R/S ratio of 1/4 and 90% isolated yield (FIG. 3). This mixture was then treated with enzyme (lipase) to enrich the optical purity.

Scheme 6. The asymmetric reduction of compound OBI-3424-5 to synthesis S-form majored compound OBI-3424-6

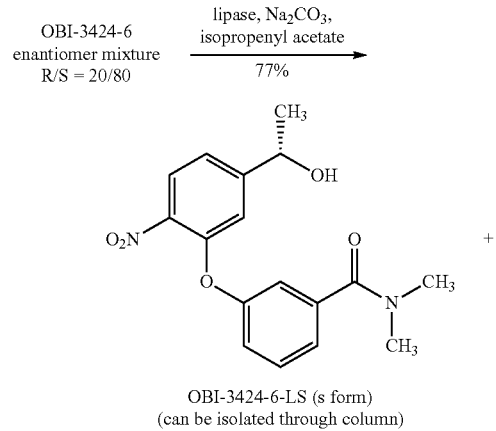

Figure 4:
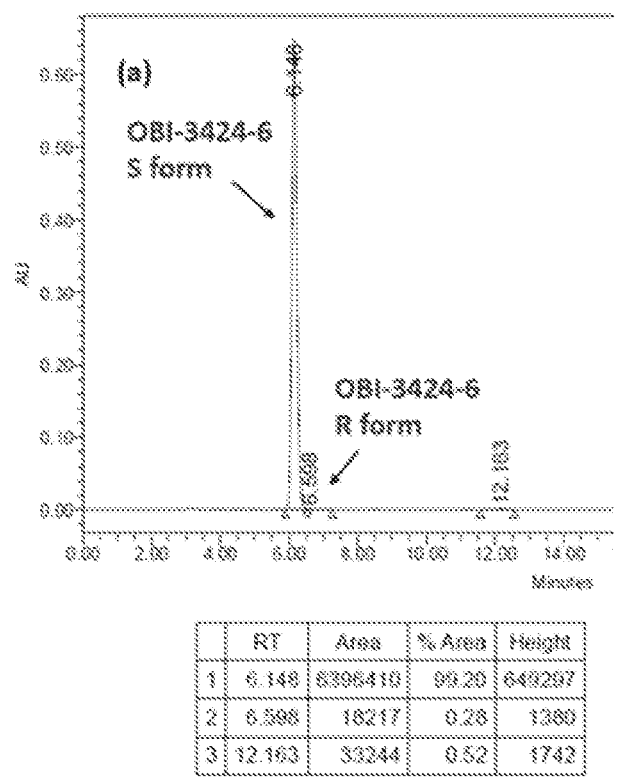
FIG. 4. The chiral HPLC analysis data of enzyme reaction of compound OBI-3424-6-LS after lipase selective esterification with compound OBI-3424-6 R/S mixture.

Step 2. Lipase Selective Acyl Protection:

To our delight, lipase could selectively acetylate R-form compound OBI-3424-6 in the R/S mixture. The passive selection and non-acetylated S-form compound OBI-3424-6 (OBI-3424-6-LS) could be obtained directly after purification. One step was omitted by comparing with compound OBI-3424-6-LR synthesis steps (removing acetyl group from compound OBI-3424-6-Ac). After simple column purification through a silica gel pad, the compound OBI-3424-6-LS could be collected with 77% yield and 99% ee value (Scheme 7, FIG. 4).

Scheme 7. The enzymatic reaction to S form compound OBI-3424-6

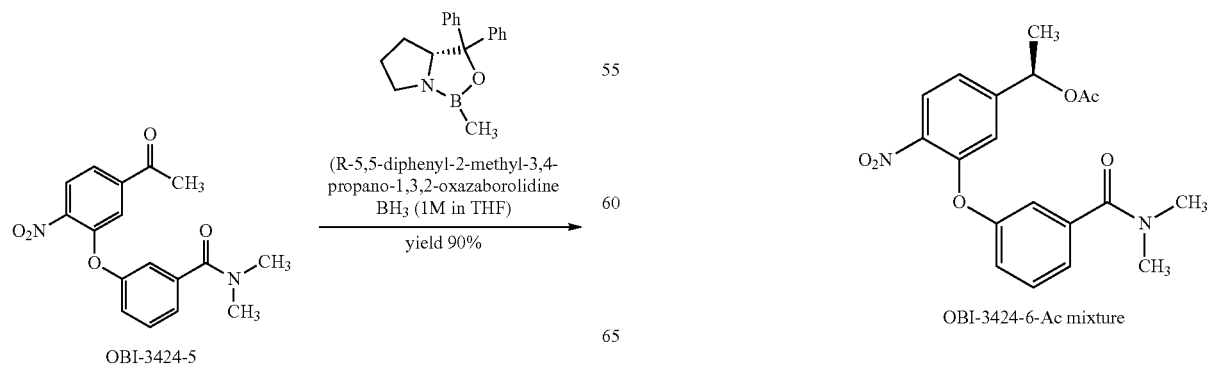

Example 5: General Synthesis of Compound OBI-3424-6 R/S Mixture

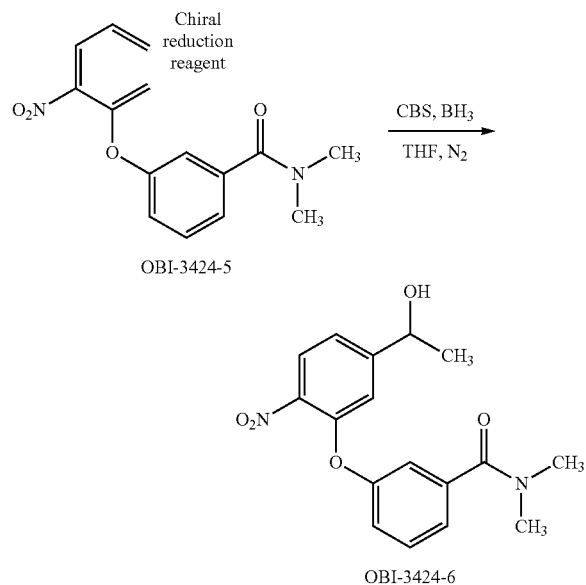

OBI-3424-5

OBI-3424-6

Mixed $BH_3$ (1 M in THF, 1.05 mol. equiv.) and CBS reagent (0.2 mol. equiv.) at 0° C. under nitrogen protection. (NOTE: two different CBS reagents were used individually, R-form majored product was obtained form (S)-5,5-diphenyl-2-methyl-3,4-propano-1,3,2-oxazaborolidine, while using of (R)-5,5-diphenyl-2-methyl-3,4-propano-1,3,2-oxazaborolidine gave s-form majored product.) After 5 min. of stirring, added compound OBI-3424-5 (1.0 mol. equiv., i.e. 0.45 g dissolved in 2 mL anhydrous THF) into the reaction. The reaction was stirring and allowed raising to 25° C. slowly under nitrogen protection. After ca. 1.5 hour stirring of addition, check TLC (volume ratio $CH_2Cl_2$/EtOAc=2/1, Rf value of compound OBI-3424-6=0.3). Upon compound OBI-3424-5 ceased, mixed reaction crude with EtOAc (4 times v/v of reaction crude) and cooled 1N HCl (25% volume of EtOAc). The reaction crude was extracted and separated. The aqueous layer was then extracted with EtOAc twice. The combined organic layer was washed with sat. $NaHCO_3$, brine, dried over $MgSO_4$, filtered, and then concentrated by the rotatory evaporator (water bath=35° C., ca. 100 mbar) to afford a yellow syrup. The resulted syrup was purified by column chromatography through a pad of silica gel. The eluent system was suggested as described below: (volume ratio packing=Hexane/EtOAc=3/1), eluent: Hexane/EtOAc=1/1 (1 column volume), $CH_2Cl_2$/EtOAc=2/1 (1 column volume), $CH_2Cl_2$/EtOAc=1/1 (3 column volume) till the expected product was collected. The collected product was concentrated by the rotatory evaporator (water bath=35° C., ca. 120 mbar) and high-vacuum (ca. 25° C., 16 hours) to afford compound OBI-3424-6 R/S mixture as a yellow syrup (ca. 90% isolated yield, R/S ratio was judged by HPLC using a chiral column).

In addition, the inventors also tested several chiral reduction reagents (e.g., DIP-Chloride, Sodium borohydrate or (S)-(−)-1,1'-Bi-2-naphthol) to replace CBS catalyst.

Procedure of (R)/(S)-Me-CBS Reagent

To a solution of different ketone substrates and (R)/(S) Me-CBS catalyst (Tokyo Chemical Industry Co., Ltd.) was cooled to 0° C. for 10 min. under nitrogen protection. Slowly added $BH_3$ (1 M in THF) (Acros Organics; Lot No.: A0400505) into the reaction and stirred for 10 min. Then the reaction mixture was stirred at room temperature for 1 hour. Upon completion, the reaction mixture was quenched with 1N HCl and water. The aqueous layer was extracted with two portions EtOAc. The collected organic layer was washed with $NaHCO_3$ and brine, dried over anhydrous $MgSO_4$, filtered, and concentrated by the rotatory evaporator to get yellow crude. The residue was purified by column chromatography through a pad of silica gel (FUJI Silysia Chemical Ltd.; Lot No. HT80186). Eluent system with the volume ratio (EtOAc/Hexane=1/4 to 3/1). The collected fractions were concentrated by the rotatory evaporator and high-vacuum to afford the product.

Procedure of (+)/(−)-DIP-Chloride Reagent

To a solution of different ketone substrates dissolved in THF (Acros Organics; Lot No.: 1850266) was cooled to 0° C. for 10 min. under nitrogen protection. (+)/(−)-DIP-Chloride (Tokyo Chemical Industry Co., Ltd.) was slowly added into the reaction and stirred for 10 min. Then the reaction mixture was stirred at room temperature for 3 hours. Upon completion, the reaction mixture was quenched with 1N HCl and MeOH. The aqueous layer was extracted with two portions EtOAc. The collected organic layer was washed with $NaHCO_3$ and brine, dried over anhydrous $MgSO_4$, filtered, and concentrated by the rotatory evaporator to get yellow crude. The residue was purified by column chromatography through a pad of silica gel (FUJI Silysia Chemical Ltd.; Cat No. HT80186). Eluent system with the volume ratio (EtOAc/Hexane=1/4 to 3/1). The collected fractions were concentrated by the rotatory evaporator and high-vacuum to afford the product.

Procedure of Sodium Borohydride ($NaBH_4$)

To a solution of different ketone substrates dissolved in MeOH at room temperature. Slowly added Sodium borohydride into the reaction. Then the reaction mixture was stirred at room temperature for 1 hour. Upon completion, the reaction mixture was quenched with water. The aqueous layer was extracted with two portions EtOAc. The collected organic layer was washed with $NaHCO_3$ and brine, dried over anhydrous $MgSO_4$, filtered, and concentrated by the rotatory evaporator to get crude. The residue was purified by column chromatography through a pad of silica gel (FUJI Silysia Chemical Ltd.; Cat No. HT80186). Eluent system with the volume ratio (EtOAc/Hexane=1/4 to 3/1). The collected fractions were concentrated by the rotatory evaporator and high-vacuum to afford the product.

Procedure of (S)-(−)-BINOL Reagent

To a solution of (S)-(−)-1,1'-Bi-2-naphthol (Tokyo Chemical Industry Co., Ltd.; Lot No.: 4HN7B-OD) and trimethylaluminum solution (Sigma-Aldrich, Inc.; Lot No. STBG1135V) was stirred at room temperature for 10 min. under nitrogen protection, after which time a white precipitate had formed. Ketone substrate 2 and 2-propanol (Tedia Company, Inc.; Lot No.: 15040128) were added into the reaction and stirred at room temperature for 16 hours. Upon completion, the reaction mixture was concentrated by rotatory evaporator to get crude. The residue was purified by column chromatography through a pad of silica gel (FUJI Silysia Chemical Ltd.; Lot No. HT80186). Eluent system with the volume ratio (EtOAc/Hexane=1/4 to 3/1). The collected fractions were concentrated by the rotatory evaporator and high-vacuum to afford the product.

Table 6 indicated the production yield by using different chiral reduction reagents of compound OBI-3424-6. It indicated CBS catalyst was the most efficient reagent for compound OBI-3424-6 synthesis. Instead, it could not produce S form or R form specific product by using NaBH$_4$.

TABLE 6

Compound OBI-3424-6 production yield by using different chiral reduction reagents

| Substrate | Reagent | | NaBH$_4$ |
|---|---|---|---|
| OBI-3424-5 | (R)-Me-CBS catalyst [CAS No.: 112068-83-0] Yield: 95% 48% ee, S form (S)-Me-CBS catalyst [CAS No.: 112022-81-8] Yield: >99% 38% ee, R form | (−)-DIP-Chloride [CAS No.: 85116-37-6] Yield: 72% 91% ee, S form (+)-DIP-Chloride [CAS No.: 112246-73-8] Yield: 54% 91% ee, R form | Yield: 85% racemic |

Furthermore, the inventors also tested several ketone substrates (see Table 7) by using R-CBS/S-CBS, (−)-DIP-Chloride/(+)-Chloride, Sodium borohydrate, or (S)-(−)-1,1'-Bi-2-naphthol. Table 7 indicated the production yield by using different ketone substrates.

TABLE 7

Enantioselective reduction of different ketone-S form major

| Substrate | Reagent | | |
|---|---|---|---|
| | (R)-Me-CBS catalyst (Yield, ee %) | (−)-DIP-Chloride (Yield, ee %) | NaBH$_4$ (Yield, ee %) |
| 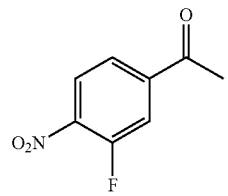 | (93%, 37% ee, S) | (71%, 87% ee, S) | (>99%, racemic) |
| 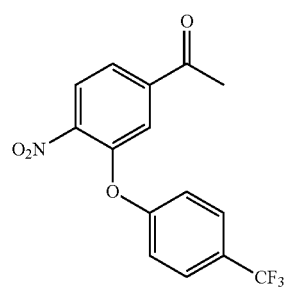 [SMILES: CC(=O)c1ccc([N+](=O)[O-])c(Oc2ccc(C(F)(F)F)cc2)c1] | (99%, 27%, ee, S) | (45%, 88% ee, S) | (>99%, racemic) |
| 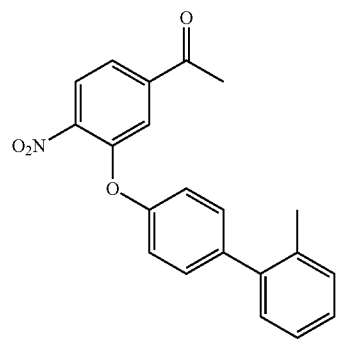 [SMILES: CC(=O)c1ccc([N+](=O)[O-])c(Oc2ccc(-c3ccccc3C)cc2)c1] | (>99%, 42% ee, S) | (62%, 91% ee, S) | (97%, racemic) |
| 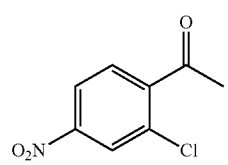 | (>99%, 27% ee, S) | (76%, 88% ee, S) | (>99%, racemic) |

TABLE 7-continued

Enantioselective reduction of different ketone-S form major

| Substrate | Reagent | | |
|---|---|---|---|
| | (R)-Me-CBS catalyst (Yield, ee %) | (−)-DIP-Chloride (Yield, ee %) | $NaBH_4$ (Yield, ee %) |
| 4-nitro-3-chloro-acetophenone | (>99%, 25% ee, S) | (62%, 90% ee, S) | (>99%, racemic) |
| 4-nitro-3-methoxy-acetophenone | (>99%, 38% ee, S) | (73%, 89% ee, S) | (96%, racemic) |
| 4-nitro-2-methoxy-acetophenone | (>99%, 60% ee, S) | (78%, 90% ee, S) | |
| acetophenone | (85%, 72% ee, S) | (>99%, 89% ee, S) | |
| 2-octanone | (82%, 12% ee, S) | (81%, racemic) | |
| 4-acetamido-acetophenone | (89%, 88% ee, S) | (82%, 87% ee, S) | |

Note:

1. The yield of Substrate 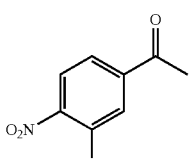 by using (S)-(−)-1,1′-Bi-2-naphthol (Tokyo Chemical Industry Co., Ltd., CAS No.: 18531-99-2) reagent was 11%, 9% ee, S form.

TABLE 7-continued

Enantioselective reduction of different ketone-S form major

| | Reagent | | |
|---|---|---|---|
| Substrate | (R)-Me-CBS catalyst (Yield, ee %) | (−)-DIP-Chloride (Yield, ee %) | NaBH₄ (Yield, ee %) |//

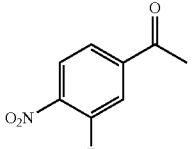

2. The yield of Substrate [structure] by using (S)-Me-CBS catalyst reagent was >99%, 34% ee, R form.

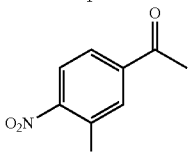

3. The yield of Substrate [structure] by using (+)-DIP-Chloride reagent was 96%, 91% ee, R form.

Example 6: Enantiomer Separation by Lipase Enzymatic Selection from Compound OBI-3426-6 R/S Mixture

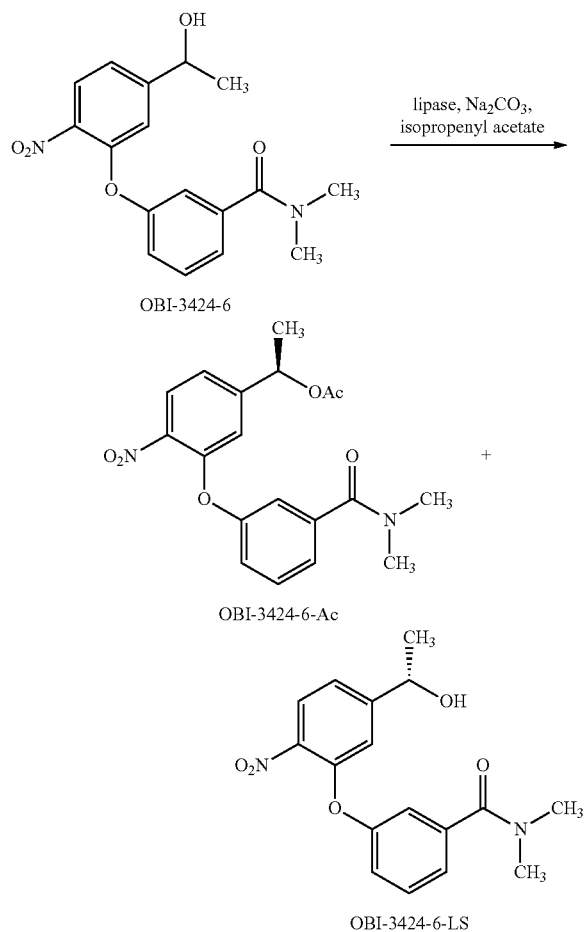

Compound OBI-3424-6 was dissolved with isopropenyl acetate to be a pre-mixture solution. Lipase (CALB) and Na₂CO₃ were added into the pre-mixture solution and put in room temperature (25° C.). Please note the reaction time is different from R-form and S-form selection (section 2.1, R-selection for 4 hours, while S-selection for 20 hours). After reaction, the upper solution was filtered (or pipetted) to remove lipase resin and shifted to a clean tube for further purification (TLC Check system=CH₂Cl₂/EtOAc/Hexane=1/2/1 volume ratio). Enzymatic reaction solution was concentrated by the rotatory evaporator (temperature of water bath=ca. 35° C., pressure=ca. 50 mbar) to afford a syrup. The syrup was then loaded on a pad of silica gel (volume ratio Hexane/EtOAc=5/1 packing), the eluent system was suggested as described below: volume ratio Hexane/EtOAc=3/1 (1 column volume), then 1/1 (1.5 column volume), then 1/4 (3 column volume), till expected product was collected; TLC Check eluent system=CH₂Cl₂/EtOAc/Hexane=1/2/1, Rf of compound OBI-3424-6-LS=0.3, Rf of compound OBI-3424-6-Ac=0.5). The compound OBI-3424-6-LS will be obtained in this step. In addition, the inventors also tested different species lipases (e.g., Lipase B from *Aspergillus oryzae* or Lipase immobilized from *Candida Antarctica*) reaction activity. To a solution of hydroxyl substrate dissolved in isopropenyl acetate (Sigma-Aldrich, Inc.; Lot No. STBH5768) at room temperature. Na₂CO₃ (Showa; Lot No. KDL-100W) and Lipase acrylic resin (Sigma-Aldrich, Inc.; Lot No. SLBW1544) or Lipase B *Candida antarctica* immobilized on Immobead 150, recombinant from *Aspergillus oryzae* (Sigma-Aldrich, Inc.; Lot No. BCBZ7604) or Lipase immobilized from *Candida antarctica* (Sigma-Aldrich, Inc.; Lot No. BCBD5551) were added into the solution. The reaction mixture was put at room temperature for 16 hours. The reaction mixture was filtered and concentrated by the rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions were concentrated by the rotatory evaporator and high-vacuum to afford the product.

In addition, the inventors also tested another reagent-2,2,2-trifluoroethyl butyrate to replace isopropenyl acetate. To a solution of hydroxyl substrate dissolved in 2,2,2-trifluoroethyl butyrate (Tokyo Chemical Industry Co., Ltd.; Lot No.: CORPC-HQ) at room temperature. $Na_2CO_3$ (Showa; Lot No. KDL-100W) and Lipase acrylic resin (Sigma-Aldrich, Inc.; Lot No. SLBW1544) were added into the solution. The reaction mixture was put at room temperature for 16 hours. The reaction mixture was filtered and concentrated by the rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions were concentrated by the rotatory evaporator and high-vacuum to afford the product. Table 8 indicated the production yield by using different lipases. It indicated that there was not a significance difference between difference species lipases.

TABLE 8

Compound OBI-3424-6-LS production yield by using different lipases

| Substrate | Lipase | | |
|---|---|---|---|
| | CALB | Lipase B from Aspergillus oryzae | Lipase from Candida Antarctica |
| OBI-3424-6 | Yield: 77% 99% ee, S form | Yield: 82% 99% ee, S form | Yield: 87% 99% ee, S form |

Note:
The yield by using 2,2,2-trifluoroethyl butyrate was 74%, 96% ee, S form.

Furthermore, the inventors also tested several substrates (see Table 9) by using different species lipases. Table 9 indicated the production yield by using lipase of several different substrates.

TABLE 9

Different lipase-catalyzed selectivity transesterification

| Substrate | Lipase | | |
|---|---|---|---|
| | CALB | Lipase B from Aspergillus oryzae | Lipase from Candida Antarctica |
| No. 2 | (61%, 99% ee, S) | (76%, 99% ee, S) | (68%, 99% ee, S) |
| No. 3 | (61%, 97% ee, S) | N/A | N/A |
| No. 4 | (81%, 98% ee, S) | | |

TABLE 9-continued

Different lipase-catalyzed selectivity transesterification

| | Lipase | | |
|---|---|---|---|
| Substrate | CALB | Lipase B from *Aspergillus oryzae* | Lipase from *Candida Antarctica* |
| No. 5 <br> 4-nitro-2-chloro-α-methylbenzyl alcohol | (72%, 85% ee, S) | | |
| No. 6 <br> 4-nitro-3-chloro-α-methylbenzyl alcohol | (59%, 99% ee, S) | | |
| No. 7 <br> 4-nitro-3-methoxy-α-methylbenzyl alcohol | (69%, 99% ee, S) | | |
| No. 8 <br> 4-nitro-2-methoxy-α-methylbenzyl alcohol | (73%, 99% ee, S) | | |
| No. 9 <br> 1-phenylethanol | (59%, 99% ee, S) | | |
| No. 10 <br> 2-octanol | (75%, racemic) | | |
| No. 11 <br> 4-acetamido-α-methylbenzyl alcohol | (95%, 98.8% ee, S) | | |

Example 7: Lipase Selectivity Hydrolysis of S-Form Major

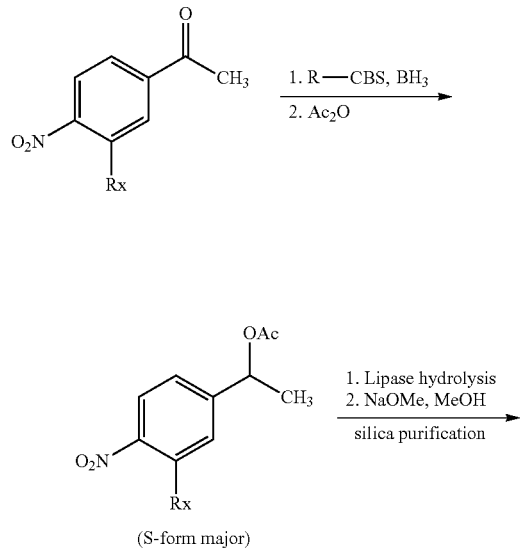

(S-form major)

(S-form 99% ee)

Step A: a solution of Acetyl substrate was dissolved in THF (Acros Organics; Lot No.: 1850266) and 0.1 M pH 7.0 potassium phosphate buffer (Sigma-Aldrich, Inc.; Lot No. MKBX6388V) at room temperature. Lipase acrylic resin (Sigma-Aldrich, Inc.; Lot No. SLBW1544) was added into the solution. The reaction mixture was put at room temperature for 16 hours. The reaction mixture was filtered and concentrated by the rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions were concentrated by the rotatory evaporator and high-vacuum to afford the product.

Step B: a solution of acetyl substrate was dissolved in MeOH (BioSuperStar Co., Ltd.; Lot No.: 14022569) at room temperature. NaOMe was added into the solution. Then the reaction mixture was stirred at room temperature for 1 hour. Upon completion, the reaction mixture was quenched with HCl (1N in MeOH) and concentrated by rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions was concentrated by the rotatory evaporator and high-vacuum to afford the product. Table 10 indicated the production yield by using lipase of acetyl substrate.

TABLE 10

Production yield by using lipase reagent of acetyl substrates

| Substrate | Step A: Lipase from CALB (Yield) | Step B: NaOMe (Yield, ee %) |
|---|---|---|
| No. 13 | 74% | 94%, 94% ee S form |
| OBI-3424-6-OAc (S-Form Major) | 94% | >99%, 56% ee S form |

Example 8: Protease Enzymatic Selection Transesterification from Compound OBI-3426-6 R/S Mixture

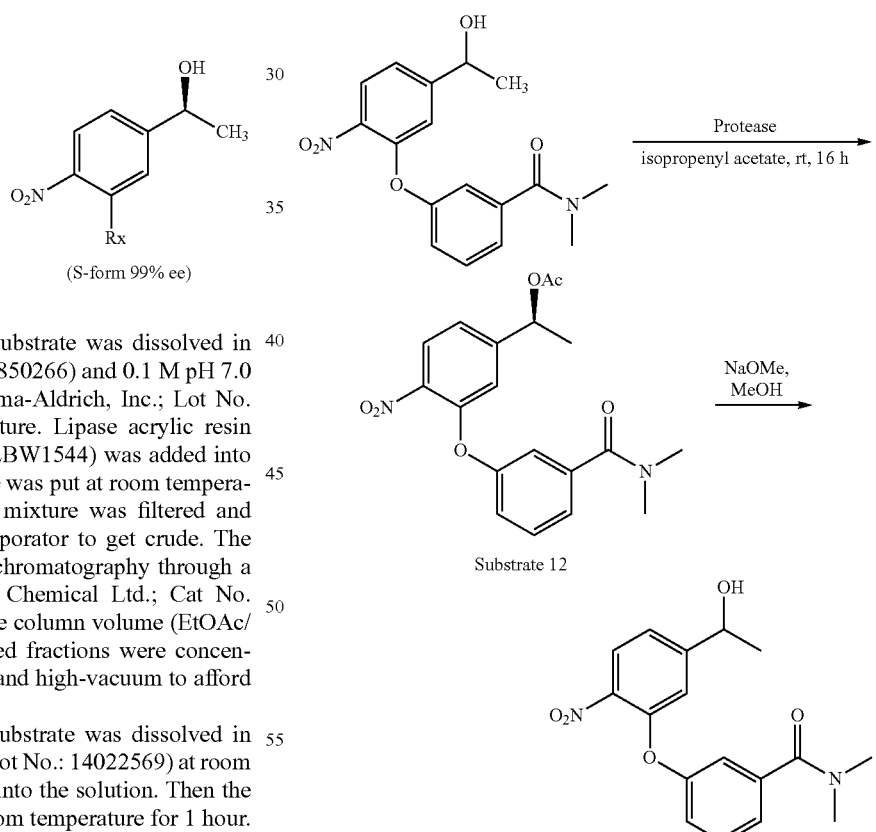

Substrate 12

Step A: a solution of Hydroxyl substrate was dissolved in 2,2,2-trifluoroethyl butyrate (Tokyo Chemical Industry Co., Ltd.; Lot No.: CORPC-HQ) at room temperature. Protease (Sigma-Aldrich, Inc., from *Bacillus licheniformis*, Lot No. SLBX1986 or from *Streptomyces griseus*, Lot No. SLCB9815) from different species was added into the solution. The reaction mixture was put at room temperature for 16 hours. The reaction mixture was filtered and concentrated by the rotatory evaporator to get crude. The residue was purified by column chromatography through a pad of silica gel (FUJI Silysia Chemical Ltd.; Cat No. SY350). Eluent system with the column volume (EtOAc/Hexane=1/4 to 3/1). The collected fractions were concentrated by the rotatory evaporator and high-vacuum to afford the product.

Step B: a solution of Acetyl substrate was dissolved in MeOH at room temperature. NaOMe was added into the solution. Then the reaction mixture was stirred at room temperature for 1 hour. Upon completion, the reaction mixture was quenched with HCl (1N in MeOH) and concentrated by rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions were concentrated by the rotatory evaporator and high-vacuum to afford the product. Table 11 indicated the production yield by using different proteases. It indicated that there were both low yield of two species lipases.

TABLE 11

Production yield by using different proteases

| Substrate | Reagent | |
|---|---|---|
| | Step A: Protease from *Bacillus licheniformis* (Yield) | Step B: NaOMe (Yield, ee %) |
| OBI-3424-6 (S-Form Major) | 11% | 50%, 99% ee S form |
| | 10% | 93%, 99% ee S form |

| Substrate | Reagent | |
|---|---|---|
| | Step A: Protease from *Streptomyces griseus* (Yield) | Step B: NaOMe (Yield, ee %) |
| OBI-3424-6 (S-Form Major) | 4% | 74%, 87% ee S form |

Example 9: Protease Selectivity Hydrolysis of S-Form Major

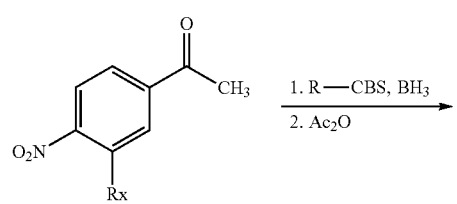

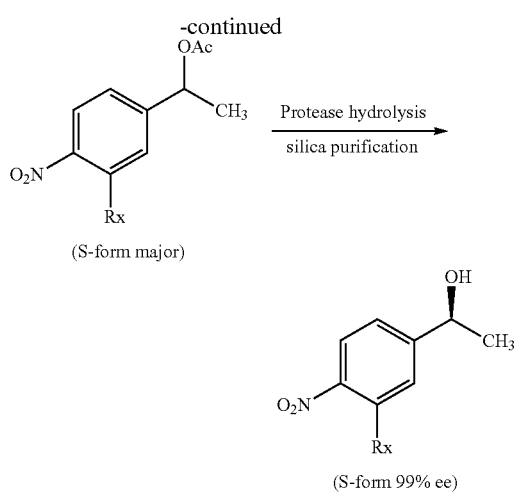

(S-form major)

(S-form 99% ee)

A solution of acetyl substrate was dissolved in ethyl ether (Avantor Performance Materials, Inc.; Lot No.: 0000128533) and 0.1 M pH 7.0 potassium phosphate buffer (Sigma-Aldrich, Inc.; Lot No. MKBX6388V) at room temperature. Protease (Sigma-Aldrich, Inc.; Protease from *Bacillus licheniformis*, Lot No. SLBX1986) was added into the solution. The reaction mixture was put at room temperature for 16 hours. The reaction mixture was filtered and concentrated by the rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions was concentrated by the rotatory evaporator and high-vacuum to afford the product. Table 12 indicated the production yield by using protease of acetyl substrate.

TABLE 12

Production yield by using protease reagent of acetyl substrates

| Substrate | Reagent Protease (Yield, ee %) |
|---|---|
| No. 13 | 6%, 27% ee S form |
| OBI-3424-6-OAc (S-Form Major) | 11%, 88% ee S form |

Example 10: Enantioselective Reduction of Ketone-R Form Major

Step A: a solution of hydroxyl substrate was dissolved in isopropenyl acetate (Sigma-Aldrich, Inc.; Lot No. STBH5768) at room temperature. Na$_2$CO$_3$ and Lipase acrylic resin (Sigma-Aldrich, Inc.; Lot No. SLBW1544) were added into the solution. The reaction mixture was put at room temperature for 16 hours. The reaction mixture was filtered and concentrated by the rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions were concentrated by the rotatory evaporator and high-vacuum to afford the product.

Step B: a solution of acetyl substrate was dissolved in MeOH at room temperature. NaOMe was added into the solution. Then the reaction mixture was stirred at room temperature for 1 hour. Upon completion, the reaction mixture was quenched with HCl (1N in MeOH) and concentrated by the rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions were concentrated by the rotatory evaporator and high-vacuum to afford the product. Table 13 indicated the production yield by using lipase reagent of acetyl substrates.

TABLE 13

Production yield by using lipase reagent of acetyl substrates

| | Reagent | |
|---|---|---|
| Substrate | Step A: CALB (Yield) | Step B: NaOMe (Yield, ee %) |
| 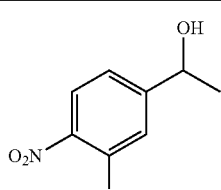 OBI-3424-6 | 70% 65% | 98%, 99% ee R form 92%, 99% ee R form |

Example 11: Lipase Selectivity Hydrolysis of R-Form Major

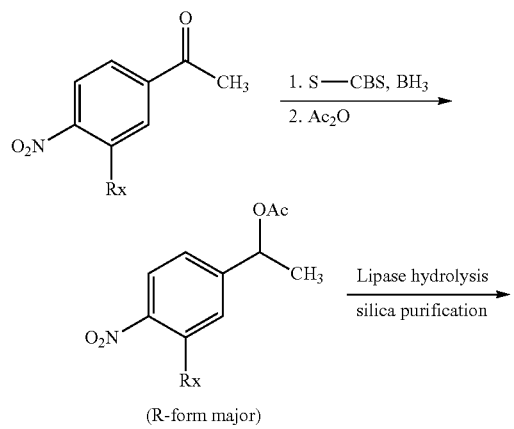

(R-form major)

-continued

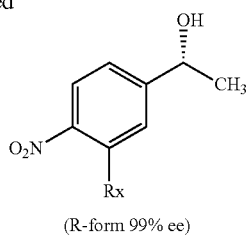

(R-form 99% ee)

A solution of acetyl substrate was dissolved in ethyl ether (Avantor Performance Materials, Inc.; Lot No.: 0000128533) and 0.1 M pH 7.0 potassium phosphate buffer at room temperature. Lipase acrylic resin (Sigma-Aldrich, Inc.; Lot No. SLBW1544) was added into the solution. The reaction mixture was put at room temperature for 16 hours. The reaction mixture was filtered and concentrated by the rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions were concentrated by the rotatory evaporator and high-vacuum to afford the product. Table 14 indicated the production yield by using lipase reagent of acetyl substrates.

TABLE 14

Production yield by using lipase reagent of acetyl substrates

| Substrate | Reagent Lipase from CALB (Yield, ee %) |
|---|---|
| No. 13 | 77%, 99% ee, R form |
| 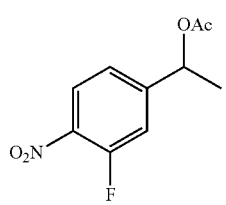 OBI-3424-6-OAc (R form major) | 56%, 99% ee, R form |

Example 12: Protease Selectivity Hydrolysis of R-Form Major

Step A: a solution of acetyl substrate was dissolved in ethyl ether (Avantor Performance Materials, Inc.; Lot No.: 0000128533) and 0.1 M pH 7.0 potassium phosphate buffer at room temperature. Protease (Sigma-Aldrich, Inc.; Protease from Bacillus licheniformis, Lot No. SLBX1986) was added into the solution, the reaction mixture was put at room temperature for 16 hours. The reaction mixture was filtered and concentrated by rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions was concentrated by the rotatory evaporator and high-vacuum to afford the product.

Step B: a solution of acetyl substrate was dissolved in MeOH at room temperature. NaOMe was added into the solution. Then the reaction mixture was stirred at room temperature for 1 hour. Upon completion, the reaction mixture was quenched with HCl (1N in MeOH) and concentrated by the rotatory evaporator to get crude. The residue was purified by column chromatography through a pad of silica gel (FUJI Silysia Chemical Ltd.; Cat No. HT80186). Eluent system with the column volume (EtOAc/Hexane=1/4 to 3/1). The collected fractions were concentrated by the rotatory evaporator and high-vacuum to afford the product. Table 15 indicated the production yield by using protease of acetyl substrate.

TABLE 15

Production yield by using protease reagent of acetyl substrates

| Substrate | Reagent | |
|---|---|---|
| | Step A: Protease (Yield) | Step B: NaOMe (Yield, ee %) |
| No. 13 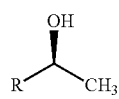 | >99% | 94%, 33% ee R form |
| OBI-3424-6-OAc (R-Form Major) | 89% | 99%, 38% ee R form |

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited herein are incorporated herein by reference to the full extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. A method for preparing a compound of Formula 1, comprising:

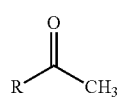

Formula 1 step (1): reacting a compound of Formula 2 with a compound of Formula 3a in the presence of $BH_3$, B-Chlorodiisopinocampheylborane (DIP-Chloride), (S)-(−)-1,1'-Bi-2-naphthol, or $NaBH_4$; and Formula 2

-continued

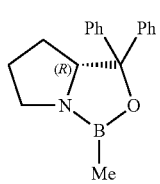

Formula 3a step (2): reacting a product of step (1) with:
(A) lipase acrylic resin, $Na_2CO_3$, and one of isopropenyl acetate and 2,2,2-trifluoroethyl butyrate; or
(B) protease, $Na_2CO_3$, and one of isopropenyl acetate and 2,2,2-trifluoroethyl butyrate; and reacting a product of step (B) with sodium methoxide in the presence of methanol, wherein R is

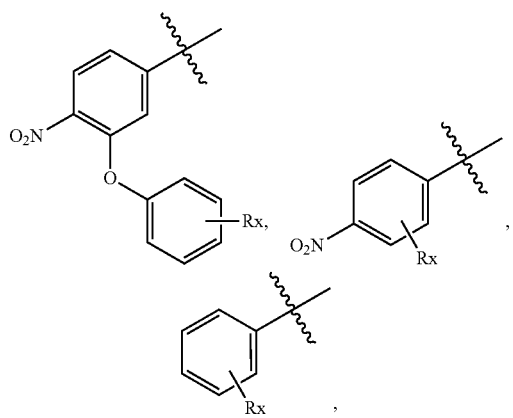

an aliphatic chain, or Rx;
wherein Rx is hydrogen, an unsubstituted or substituted cyclic ring group, an electron withdrawing group, or an electron donating group.

2. The method of claim 1, wherein the cyclic ring group is an aromatic group, a cyclic saturated or partially unsaturated group, or a heterocyclic ring group; the electron withdrawing group is a halo, nitroso, aminocarbonyl, carboxyl, alkoxycarbonyl, formyl, acyl, haloformyl, trihalomethyl, cyano, nitro, ammonium group, azide, or sulfonyl group; and the electron donating group is an alkyl, vinyl, phenyl, acyloxyl, acylamido, alkylthio, sulfhyfryl, hydroxyl, alkoxy, or amino group.

3. The method of claim 1, wherein the compound of Formula 1 is a compound of Formula OBI-3424-6-LS, and the compound of Formula 2 is a compound of Formula OBI-3424-5:

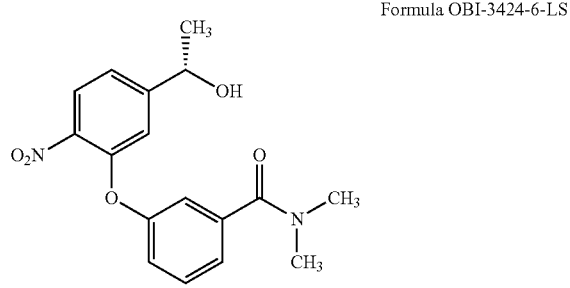

Formula OBI-3424-6-LS

Formula OBI-3424-5

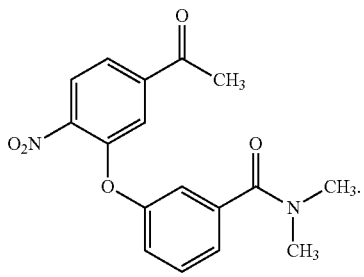

4. The method of claim 3, wherein the product of step (1) is a compound of Formula 5:

Formula 5

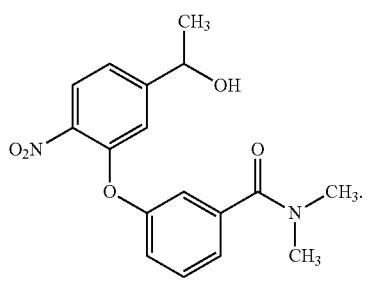

5. A method for preparing a compound of Formula 1, comprising:

Formula 1

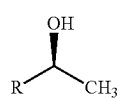

step (1a): reacting a compound of Formula 2 with a compound of Formula 3a in the presence of $BH_3$, DIP-Chloride, (S)-(−)-1,1'-Bi-2-naphthol, or $NaBH_4$;

Formula 2

R—C(O)—CH₃

Formula 3a

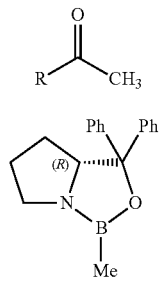

step (1b): reacting a product of step (1a) with acetic anhydride ($Ac_2O$); and step (2): reacting a product of step (1b) with:
(A) lipase acrylic resin, and $Na_2CO_3$; and reacting a product of step (A) with sodium methoxide in the presence of methanol; or
(B) protease, and $Na_2CO_3$, wherein R is

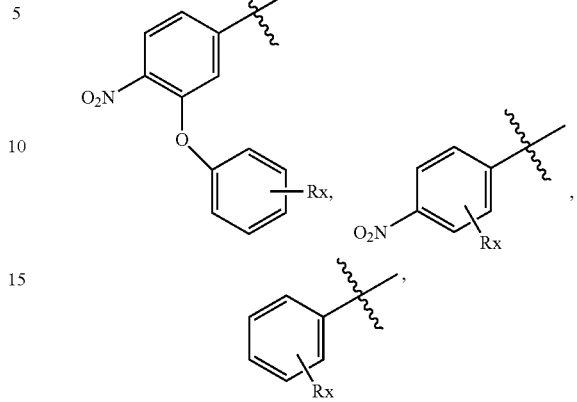

an aliphatic chain, or Rx;
wherein Rx is hydrogen, an unsubstituted or substituted cyclic ring group, an electron withdrawing group, or an electron donating group.

6. The method of claim 5, wherein the cyclic ring group is an aromatic group, a cyclic saturated or partially unsaturated group, or a heterocyclic ring group; the electron withdrawing group is a halo, nitroso, aminocarbonyl, carboxyl, alkoxycarbonyl, formyl, acyl, haloformyl, trihalomethyl, cyano, nitro, ammonium group, azide, or sulfonyl group; and the electron donating group is an alkyl, vinyl, phenyl, acyloxyl, acylamido, alkylthio, sulfhyfryl, hydroxyl, alkoxy, or amino group.

7. The method of claim 5, wherein the compound of Formula 1 is a compound of Formula OBI-3424-6-LS, and the compound of Formula 2 is a compound of Formula OBI-3424-5:

Formula OBI-3424-6-LS

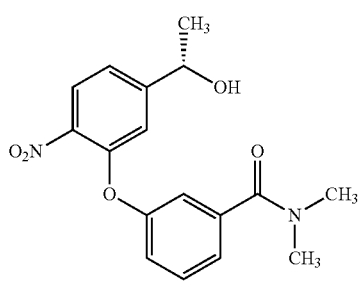

Formula OBI-3424-5

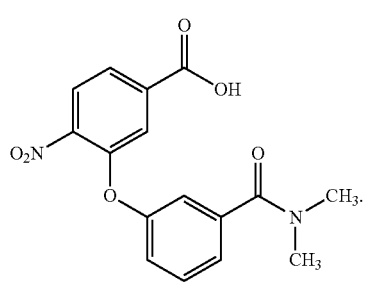

8. The method of claim 7, wherein the product of step (1b) is a compound of Formula 6:

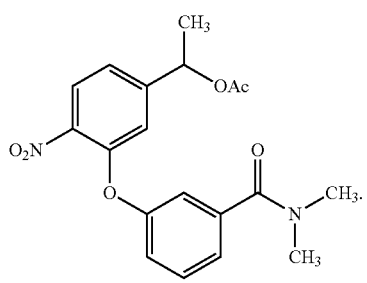

Formula 6

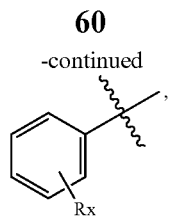

-continued an aliphatic chain, or Rx;

wherein Rx is hydrogen, an unsubstituted or substituted cyclic ring group, an electron withdrawing group, or an electron donating group.

9. A method for preparing a compound of Formula 4, comprising:

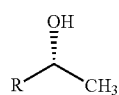

Formula 4 step (1): reacting a compound of Formula 2 with a compound of Formula 3b in the presence of $BH_3$, DIP-Chloride, (S)-(–)-1,1'-Bi-2-naphthol, or $NaBH_4$; and

10. The method of claim 9, wherein the cyclic ring group is an aromatic group, a cyclic saturated or partially unsaturated group, or a heterocyclic ring group; the electron withdrawing group is a halo, nitroso, aminocarbonyl, carboxyl, alkoxycarbonyl, formyl, acyl, haloformyl, trihalomethyl, cyano, nitro, ammonium group, azide, or sulfonyl group; and the electron donating group is an alkyl, vinyl, phenyl, acyloxyl, acylamido, alkylthio, sulfhyfryl, hydroxyl, alkoxy, or amino group.

11. The method of claim 9, wherein the compound of Formula 4 is a compound of Formula OBI-3424-6-LR, and the compound of Formula 2 is a compound of Formula OBI-3424-5:

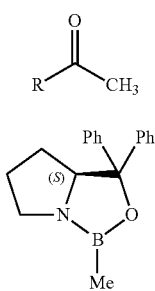

Formula 2

Formula 3b step (2): reacting a product of step (1) with:
(A) lipase acrylic resin, $Na_2CO_3$, and one of isopropenyl acetate and 2,2,2-trifluoroethyl butyrate; and reacting a product of step (A) with sodium methoxide in the presence of methanol; or
(B) protease, $Na_2CO_3$, and one of isopropenyl acetate and 2,2,2-trifluoroethyl butyrate, wherein R is

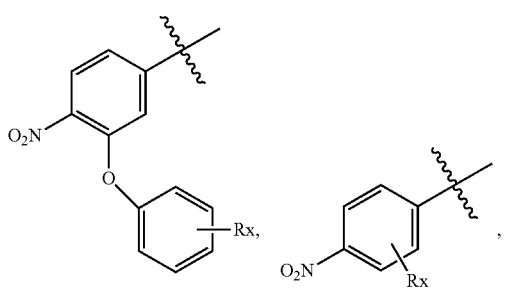

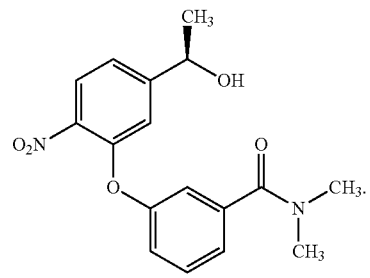

Formula OBI-3424-6-LR

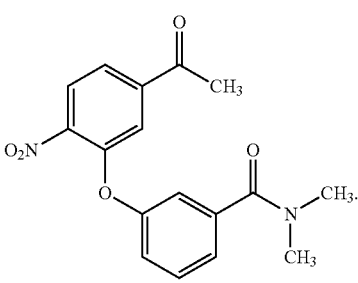

Formula OBI-3424-5

12. The method of claim 11, wherein the product of step (1) is a compound of Formula 5:

Formula 5

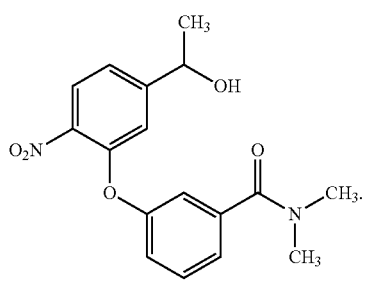

13. A method for preparing a compound of Formula 4, comprising:

Formula 4

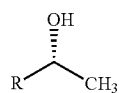

step (1a): reacting a compound of Formula 2 with a compound of Formula 3b in the presence of BH₃, DIP-Chloride, (S)-(−)-1,1'-Bi-2-naphthol, or NaBH₄;

Formula 2

R$\underset{\text{O}}{\overset{}{\text{—C—}}}$CH₃

Formula 3b

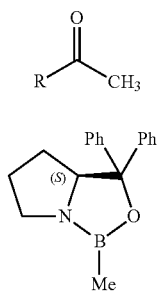

step (1b): reacting a product of step (1a) with acetic anhydride (Ac₂O); and step (2): reacting a product of step (1b) with:
(A) lipase acrylic resin, and Na₂CO₃; or
(B) protease, and Na₂CO₃; and reacting a product of step (B) with sodium methoxide in the presence of methanol wherein R is

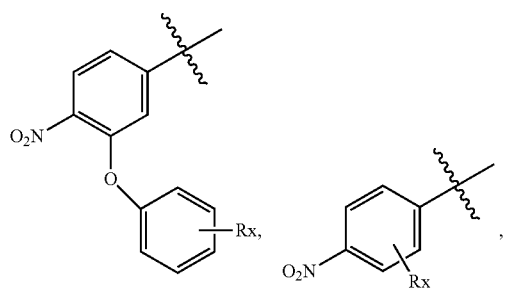

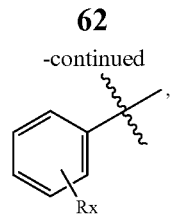

an aliphatic chain, or Rx;

wherein Rx is hydrogen, an unsubstituted or substituted cyclic ring group, an electron withdrawing group, or an electron donating group.

14. The method of claim 13, wherein the cyclic ring group is an aromatic group, a cyclic saturated or partially unsaturated group, or a heterocyclic ring group; the electron withdrawing group is a halo, nitroso, aminocarbonyl, carboxyl, alkoxycarbonyl, formyl, acyl, haloformyl, trihalomethyl, cyano, nitro, ammonium group, azide, or sulfonyl group; and the electron donating group is an alkyl, vinyl, phenyl, acyloxy, acylamido, alkylthio, sulfhyfryl, hydroxyl, alkoxy, or amino group.

15. The method of claim 13, wherein the compound of Formula 4 is a compound of Formula OBI-3424-6-LR, and the compound of Formula 2 is a compound of Formula OBI-3424-5:

Formula OBI-3424-6-LR

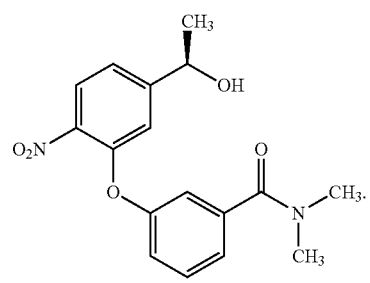

Formula OBI-3424-5

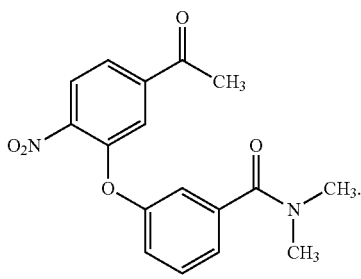

16. The method of claim 15, wherein the product of step (1b) is a compound of Formula 6:

Formula 6

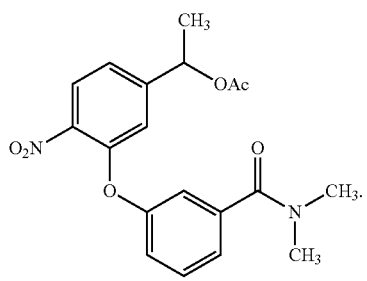

Formula OBI-3424

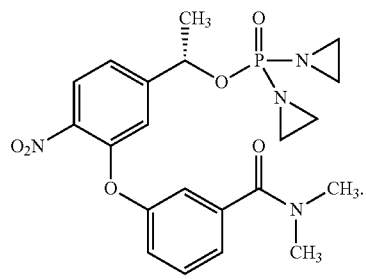

17. The method of claim 3, wherein the compound of Formula OBI-3424-5 is obtained by a compound of Formula OBI-3424-3 reacted with a compound of Formula OBI-3424-4 and $Cs_2CO_3$; the compound of Formula OBI-3424-3 is obtained by a compound of Formula OBI-3424-1 reacted with $SOCl_2$, dimethyl manolate, $MgCl_2$, and HCl; and wherein the compound of Formula OBI-3424-6-LS is used to prepare a compound of Formula OBI-3424-7 by reacting with $POCl_3$, triethylamine, and $H_2NCH_2CH_2Br$, and a compound of Formula OBI-3424 is obtained by the compound of Formula OBI-3424-7 reacted with $Ag_2O$, 18. The method of claim 7, wherein the compound of Formula OBI-3424-5 is obtained by a compound of Formula OBI-3424-3 reacted with a compound of Formula OBI-3424-4 and $Cs_2CO_3$; the compound of Formula OBI-3424-3 is obtained by a compound of Formula OBI-3424-1 reacted with $SOCl_2$, dimethyl manolate, $MgCl_2$, and HCl; and wherein the compound of Formula OBI-3424-6-LS is used to prepare a compound of Formula OBI-3424-7 by reacting with $POCl_3$, triethylamine, and $H_2NCH_2CH_2Br$, and a mixture of a compound of Formula OBI-3424 is obtained by the compound of Formula OBI-3424-7 reacted with $Ag_2O$, Formula OBI-3424-1

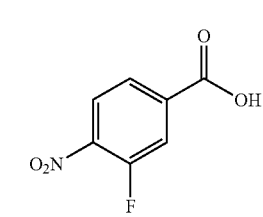

Formula OBI-3424-1

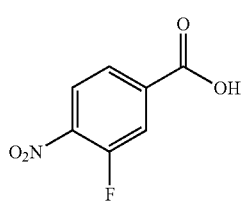

Formula OBI-3424-3

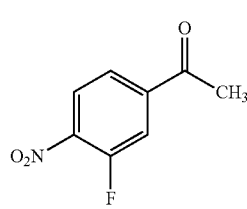

Formula OBI-3424-3

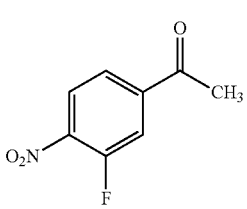

Formula OBI-3424-4

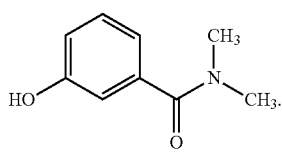

Formula OBI-3424-4

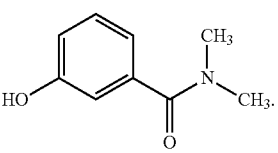

Formula OBI-3424-7

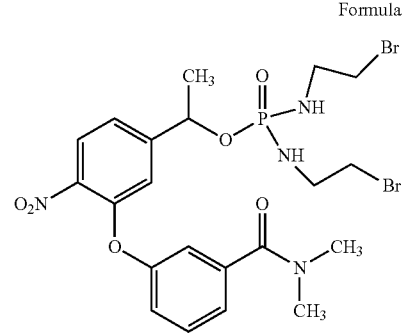

Formula OBI-3424-7

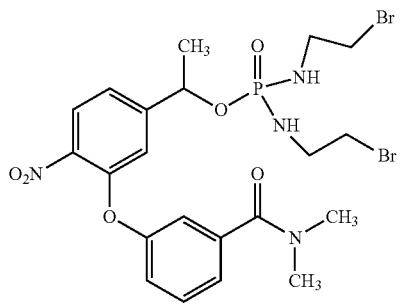

Formula OBI-3424

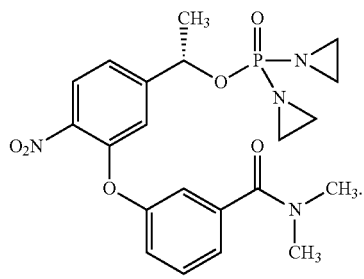

Formula OBI-3423

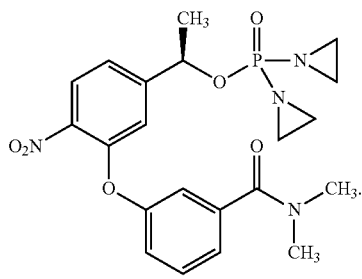

19. The method of claim 11, wherein the compound of Formula OBI-3424-5 is obtained by a compound of Formula OBI-3424-3 reacted with a compound of Formula OBI-3424-4 and Cs$_2$CO$_3$; the compound of Formula OBI-3424-3 is obtained by a compound of Formula OBI-3424-1 reacted with SOCl$_2$, dimethyl manolate, MgCl$_2$, and HCl; and wherein the compound of Formula OBI-3424-6-LR is used to prepare a compound of Formula OBI-3424-7 by reacting with POCl$_3$, triethylamine, and H$_2$NCH$_2$CH$_2$Br, and a compound of OBI-3423 is obtained by the compound of Formula OBI-3424-7 reacted with Ag$_2$O, 20. The method of claim 15, wherein the compound of Formula OBI-3424-5 is obtained by a compound of Formula OBI-3424-3 reacted with a compound of Formula OBI-3424-4 and Cs$_2$CO$_3$; the compound of Formula OBI-3424-3 is obtained by a compound of Formula OBI-3424-1 reacted with SOCl$_2$, dimethyl manolate, MgCl$_2$, and HCl; and wherein the compound of Formula OBI-3424-6-LR is used to prepare a compound of Formula OBI-3424-7 by reacting with POCl$_3$, triethylamine, and H$_2$NCH$_2$CH$_2$Br, and a compound of OBI-3423 is obtained by the compound of Formula OBI-3424-7 reacted with Ag$_2$O, Formula OBI-3424-1

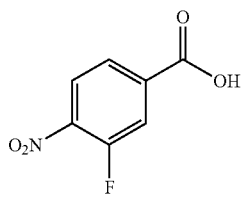

Formula OBI-3424-1

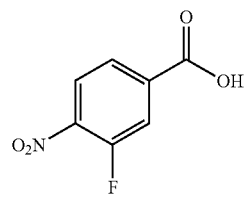

Formula OBI-3424-3

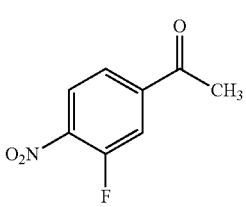

Formula OBI-3424-3

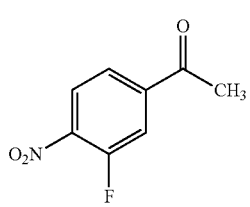

Formula OBI-3424-4

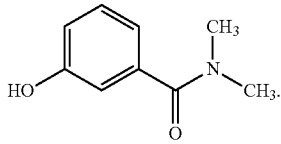

Formula OBI-3424-4

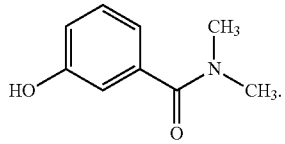

Formula OBI-3424-7

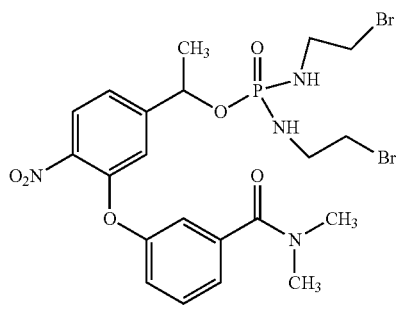

Formula OBI-3424-7

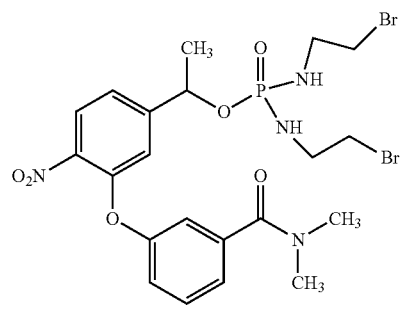

-continued
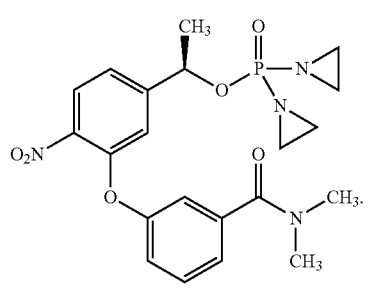
Formula OBI-3423
* * * * *